US012799519B2

(12) United States Patent
Xu et al.

(10) Patent No.: US 12,799,519 B2
(45) Date of Patent: Nov. 17, 2026

(54) METHOD TO VERIFY THE EFFECTIVENESS OF A STERILIZATION PROCESS BASED ON THE PRESENCE OF VOLATILE ORGANIC COMPOUNDS

(71) Applicants: O&M Halyard, Inc., Mechanicsville, VA (US); Georgia Tech Research Corporation, Atlanta, GA (US)

(72) Inventors: Jie Xu, Marietta, GA (US); Sylvie Dufresne, Quebec (CA); Stephanie C. Richter, Atlanta, GA (US); Anthony S. Spencer, Woodstock, GA (US)

(73) Assignees: O&M Halyard, Inc., Glen Allen, VA (US); Georgia Tech Research Corporation, Atlanta, GA (US)

( * ) Notice: Subject to any disclaimer, the term of this patent is extended or adjusted under 35 U.S.C. 154(b) by 398 days.

(21) Appl. No.: 18/477,973

(22) Filed: Sep. 29, 2023

(65) Prior Publication Data

US 2024/0110217 A1 Apr. 4, 2024

Related U.S. Application Data

(60) Provisional application No. 63/411,990, filed on Sep. 30, 2022.

(51) Int. Cl.
*C12Q 1/22* (2006.01)
*G01N 33/00* (2006.01)

(52) U.S. Cl.
CPC ........... *C12Q 1/22* (2013.01); *G01N 33/0027* (2013.01)

(58) Field of Classification Search
CPC .............................. C12Q 1/22; G01N 33/0027
See application file for complete search history.

(56) References Cited

U.S. PATENT DOCUMENTS

| | | | | |
|---|---|---|---|---|
| 6,764,832 | B2 | 7/2004 | Restaino | |
| 8,127,593 | B2 | 3/2012 | Moularat | |
| 8,318,452 | B2 | 11/2012 | Rambach | |
| 8,410,562 | B2 | 4/2013 | Lazarus et al. | |
| 8,736,000 | B1 | 5/2014 | Manginell et al. | |
| 10,077,464 | B2 | 9/2018 | Cellier et al. | |
| 10,876,144 | B2 | 12/2020 | Centanni et al. | |
| 10,889,848 | B2 | 1/2021 | Franciskovich et al. | |
| 10,900,062 | B2 | 1/2021 | Franciskovich et al. | |
| 2003/0049718 | A1 | 3/2003 | Restaino | |
| 2008/0145879 | A1 | 6/2008 | Orenga et al. | |
| 2009/0280524 | A1 | 11/2009 | Rambach | |
| 2011/0180884 | A1 | 7/2011 | Lazarus et al. | |
| 2015/0329897 | A1 | 11/2015 | Cellier et al. | |
| 2019/0017092 | A1* | 1/2019 | Franciskovich | C12Q 1/22 |
| 2019/0106726 | A1 | 4/2019 | Cregger et al. | |
| 2021/0311002 | A1 | 10/2021 | Ahimou et al. | |

FOREIGN PATENT DOCUMENTS

| | | | | |
|---|---|---|---|---|
| CN | 112 156 217 | A | 1/2021 | |
| EP | 0 152 298 | A2 | 8/1985 | |
| EP | 0433053 | A1 * | 6/1991 | C12Q 1/22 |
| EP | 3 408 405 | B1 | 6/2020 | |
| WO | WO 2008/082728 | A2 | 7/2008 | |
| WO | WO 2008/125770 | A1 | 10/2008 | |
| WO | WO 2019/014313 | A1 | 1/2019 | |
| WO | WO 2019/014316 | A1 | 1/2019 | |
| WO | WO 2019/074639 | A1 | 4/2019 | |

OTHER PUBLICATIONS

Senecal, Andre G., et al. "Rapid detection of pathogenic bacteria by volatile organic compound (VOC) analysis." Chemical and Biological Early Warning Monitoring for Water, Food, and Ground. vol. 4575. SPIE, 2002. (Year: 2002).*

Cheung, William. Metabolic profiling of volatile organic compounds and enhanced vibrational spectroscopy. The University of Manchester (United Kingdom), 2011. (Year: 2011).*

Kluger, Bernhard, et al. "Detection and identification of fungal microbial volatile organic compounds by HS-SPME-GC-MS." Laboratory protocols in fungal biology: current methods in fungal biology. New York, NY: Springer New York, 2012. 455-465. (Year: 2012).*

Khalid et al., "A Survey on Battery-Less RFID-Based Wireless Sensors", Micromachines, vol. 12, No. 7, Jul. 13, 2021, 26 pages.

Busman et al., "Volatile Organic Compound Profile Fingerprints Using DART-MS Shows Species-Specific Patterns in *Fusarium* Mycotoxin Producing Fungi", Journal of Fungi, vol. 8. No. 1, Dec. 21, 2021, 18 pages.

International Search Report & Written Opinion for PCT/US2023/034123, dated Dec. 22, 2023, 12 pages.

Albert et al., "Biological indicators for steam sterilization: characterization of a rapid biological indicator utilizing *Bacillus stearothermophilus* spore-associated alpha-glucosidase enzyme", Journal of Applied Microbiology, vol. 85, 1998 10 pages.

Altaee et al., "Characterization of Metabolites Produced by *E. coli* and Analysis of Its Chemical Compounds Using GC-MS", International Journal of Current Pharmaceutical Review and Research, vol. 7, Dec. 2016, 7 pages.

(Continued)

*Primary Examiner* — Robert J Yamasaki
*Assistant Examiner* — Trevor Kane
(74) *Attorney, Agent, or Firm* — Dority & Manning, P.A.

(57) ABSTRACT

A method for determining if a spore in a self-contained biological indicator is in a germination phase is provided. The method includes subjecting a self-contained biological indicator to a sterilization process; exposing spores in the self-contained biological indicator to a growth medium; incubating the spores in the self-contained biological indicator; sampling headspace in the self-contained biological indicator; and determining if a volatile organic compound attributable to the germination phase of the spores in the biological indicator is released into headspace upon contact with the growth medium, wherein the presence of the volatile organic compound attributable to the germination phase of the spores in the self-contained biological indicator indicates failure of the sterilization process. A method for determining if a sterilization process was successful or was a failure by measuring VOC concentration is also provided.

16 Claims, 27 Drawing Sheets

(56) References Cited

OTHER PUBLICATIONS

Altaee et al., "Detection of Volatile Compounds Produced by *Pseudomonas aeruginosa* Isolated from UTI Patients by Gas Chromatography—Mass Spectrometry", International Journal of Current Pharmaceutical Review and Research, vol. 8, Dec. 2016, 9 pages.
Billington et al., "Isolation of the Putative Intermediate 4-Methylthio-2-Oxobutanoate from Culture Fluids of Bacteria and Fungi", Biochem. J., vol. 182, 1979, pp. 827-836.
Blake et al., "Immunomagnetic Detection of *Bacillus stearothermophilus* Spores in Food and Environmental Samples", Applied and Environmental Microbiology, vol. 63, No. 5,May 1997, pp. 1643-1646.
Boland et al., "Complete spore-cortex hydrolysis during germination of *Bacillus subtilis* 168 requires SleB and YpeB", Microbiology, vol. 146, 2000, pp. 57-64.
Bressuire-Isoard, et al., "Sporulation environment influences spore properties in *Bacillus*: evidence and insights on underlying molecular and physiological mechanism", FEMS Microbiology Revies, vol. 42, No. 5, 2018 pp. 614-626.
Cernosek et al., "Volatile Organic Compound Profiling from Postmortem Microbes using Gas Chromatography—Mass Spectrometry", Journal of Forensic Sciences, vol. 65. No. 1, Jan. 2020, 11 pages.
Chandrapati et al., "Inducible β-glucosidase synthesis during germination and outgrowth of *Bacillus subtilis* ATCC 9372 spores", Letters in Applied Microbiology, vol. 36, 2003, pp. 15-19.
Coleman et al., "How Moist Heat Kills Spores of *Bacillus subtilis*", Journal of Bacteriology, vol. 189, No. 23, Dec. 2007, pp. 8458-8466.
Cortezzo, et al., "Analysis of factors that influence the sensitivity of spores of *Bacillus subtilis* to DNA damaging chemicals", Journal of Applied Microbiology, vol. 98, 2005, pp. 606-617.
Cortezzo et al., "Treatment with oxidizing agents damages the inner membrane of spores of *Bacillus subtilis* and sensitizes spores to subsequent stress", Journal of Applied Microbiology, vol. 97, 2004, pp. 838-852.
Cowan et al., "Lipids in the inner membrane of dormant spores of *Bacillus* species are largely immobile". PNAS, vol. 101, No. 20, May 18, 2004, pp. 7733-7738.
Dadd et al., "Germination of spores of *Bacillus subtilis* var. *niger* following exposure to gaseous ethylene oxide", Journal of Applied Bacteriology, vol. 60, 1986, 5 pages.
Dills et al., "An Evaluation of Respiration Chain-Associated Functions During Initiation of Germination of *Bacillus megaterium* Spores", Biochimica et Biophysica Acta, vol. 541, 1978, pp. 301-311.
Elsden et al., "Volatile acid production from threonine, valine, leucine and isoleucine by clostridia", Archives of Microbiology, vol. 177, 1978, 1 page.
Francis et al., "Detecting Cortex Fragments During Bacterial Spore Germination", Journal of Visualized Experiments, Jun. 2016, 7 pages.
Fukushima et al., "A Polysaccharide Deacetylase Gene (pdaA) Is Required for Germination and for Production of Muramic δ-Lactam Residues in the Spore Cortex of *Bacillus subtilis*", Journal of Bacteriology, vol. 184, No. 21, Nov. 2002, pp. 6007-6015.
Gao et al., "Identification of endophytic *Bacillus velezensis* ZSY-1 strain and antifungal activity of its volatile compounds against *Alternaria solani* and *Botrytis cinerea*", Biological Control, vol. 105, 2017, pp. 27-39.
Goldman et al., "Pathways of Glucose Catabolismin *Bacillus cereus*", Journal of Bacteriology, vol. 87, No. 2, Feb. 1064, pp. 377-386.
Hachisuka, et al., "Studies on Spore Germination", Effect of Nitrogen Sources on Spore Germination, vol. 69, Sep. 24, 1954, pp. 399-406.
Hagen et al., "Survival of Microorganisms in a Simulated Martian Environment", Applied Microbiology, vol. 15, No. 2, Mar. 1967, pp. 285-291.
Hills, G.M., "Chemical Factors in the Germination of Spore-bearing Aerobes. The Effects of Amino-acids on the Germination of *Bacillus anthracis*, with some Observations on the Relation of Optical Form to Biological Activity", Microbiological Research Department, vol. 45, 1950, 8 pages.
Huesca-Espitia et al., "Effects of steam autoclave treatment on *Geobacillus stearothermophilus* spores", Journal of Applied Microbiology, vol. 121, 2016, pp. 1300-1311.
Kanda et al., "Germination-initiating Activities for *Bacillus subtilis* Spores of Analogues of $_L$-Alanine Derived by Modification a the Amino or Carboxyl Group", Journal of General Microbiology, vol. 134, 1988, pp. 2747-2755.
Korza et al., "Levels of L-malate and other low molecular weight metabolites in spores of *Bacillus* species and *Clostridium difficle*", PLOS One, Aug. 29, 2017, 11 pages.
Leggett et al., "Bacterial spore structures and their protective role in biocide resistance", Journal of Applied Microbiology, vol. 113, 2012, pp. 485-498.
Magge et al., "Role of Dipicolinic Acid in the Germination, Stability and Viability of Spores of *Bacillus subtilis*", Journal of Bacteriology, vol. 190, No. 14, Jul. 2008, pp. 4798-4807.
Maruyama et al., "Glucose Catabolismuring Germination of *Bacillus megaterium* Spores", Journal of Bacteriology, vol. 141, No. 3, Mar. 1980, pp. 1443-1446.
Mckenney et al., "The *Bacillus subtilis* endospore: assembly and functions of the multilayered coat", Nature Review, Microbiology, vol. 11, Jan. 2013, 13 pages.
Melly et al., "Studies on the mechanism of killing of *Bacillus subtilis* spores by hydrogen peroxide", Journal of Applied Microbiology, vol. 93, 2002, pp. 316-325.
Moir et al., "Spore Germination", American Society for Microbiology, 2016, 20 pages.
Nitta et al., "$_L$-Amino Acid Dehydrogenases in *Bacillus subtilis* Spores", Journal of Bacteriology, vol. 117, No. 2, Feb. 1974, pp. 588-592.
Orlowski et al., "Inactivation of Glucose 6-Phosphate Dehydrogenase during Germination and Outgrowth of *Bacillus cereus* T Endospores", Biochem. J., vol. 148, 1975, pp. 259-268.
Paidhungat et al., "Spore Germination and Outgrowth", Sep. 13, 2001, 13 pages.
Popham et al., "Muramic lactam in peptidoglycan of *Bacillus subtilis* spores is required for spore growth but not for spore dehydration or heat resistance". Proc. Natl. Acad. Sci. USA, vol. 93, Dec. 1996, pp. 15405-15410.
Popham, D.L., "Specialized peptidoglycan of the bacterial endospore: the inner wall of the lockbox", CMLS Cellular and Molecular Life Sciences, vol. 59, 2002, pp. 426-433.
Popham et al., "Spore Peptidoglycan", Microbiology Spectrum, American Society for Microbiology Press, Dec. 18, 2015, 21 pages.
Prasad, Chandon, "Initiation of Spore Germination in *Bacillus subtilis*: Relationship to Inhibition of $_L$-Alaine Metabolism", Journal of Bacteriology, vol. 119, No. 3, Sep. 1974, pp. 805-810.
Prasad et al., "Initiation of Spore Germination in Glycolytic Mutants of *Bacillus subtilis*", Journal of Bacteriology, vol. 110, No. 1, Apr. 1972, pp. 321-328.
Robinson et al., "Solid-state fermentation: a promising microbial technology for secondary metabolite production", Appl., Microbiol. Biotechbol., vol. 55, 2001, pp. 284-289.
Russell, A.D., "Bacterial Spores and Chemical Sporicidal Agents", Clinical Microbiology Reviews, vol. 3, No. 2, Apr. 1990, pp. 99-119.
Rutala et al., "Guideline for Disinfection and Sterilization in Healthcare Facilities, 2008", https://www.cdc.gov/infectioncontrol/pdf/guidelines/disinfection-guidelines-H.pdf.
Ryu et al., "Bacterial Volatile Compounds as Mediators of Airborne Interactions", https://doi.org/10.1007/978-981-15-7293-7_1.
Sangavai C., "Amino acid catabolism-directed biofuel production in *Clostridium sticklandii*: An insight into model-driven systems engineering", Biotechnology Reports, vol. 16, 2017, pp. 32-43.
Santo et al., "Ultrastructural Analysis During Germination and Outgrowth of *Bacillus subtilis* Spores", Journal of Bacteriology, vol. 120, No. 1, Oct. 1974, pp. 475-481.

(56) References Cited

OTHER PUBLICATIONS

Sella et al., "Life cycle and spore resistance of spore-forming *Bacillus astrophaeus*", Microbiological Research, vol. 169, 2014, pp. 931-939.

Setlow et al., "Analysis of a-glucosidase enzyme activity used in a rapid test for steam steri I ization assurance", Journal of Applied Microbiology, vol. 120, 2016, pp. 1326-1335.

Setlow et al., "Analysis of the germination kinetics of individual *Bacillus subtilis* spores treated with hydrogen peroxide or sodium hypochlorite", Letters in Applied Microbiology, vol. 57, 2013, pp. 259-265.

Setlow et al., "Biochemical Studies of Bacterial Sporulation and Germination", The Journal of Biological Chemistry, vol. 245, No. 14, 1970, 8 pages.

Setlow et al., "Germination of Spores of the Orders *Bacillales* and *Clostridiales*", Annual Review of Microbiology, vol. 71, 2017, 22 pages.

Setlow et al., "Levels of Oxidized and Reduced Pyridine Nucleotides in Dormant Spores and During Growth, Sporulation, and Spore Germination of *Bacillus megaterium*", Journal of Bacteriology, vol. 129, No. 2, Feb. 1977, pp. 857-865.

Setlow et al., "Protein Metabolism during Germination of *Bacillus megaterium* Spores", The Journal of Biological Chemistry, vol. 250, No. 2, 1975, pp. 623-630.

Setlow, Peter, "Small, Acid-Soluble Spore Proteins of *Bacillus* Species: Structure, Synthesis, Genetics, Function and Degradation", Annual Review Microbiol., vol. 42, 1988, 20 pages.

Setlow, P., "Spores of *Bacillus subtilis*: their resistance to and killing by radiation, heat and chemicals", Journal of Applied Microbiology, vol. 101, 2006, pp. 514-525.

Sinai et al., "The Molecular Timeline of a Reviving Bacterial Spore", Molecular Cell, vol. 57, Feb. 19, 2015, pp. 695-707.

Stöver et al., "Regulation of Synthesis of the *Bacillus subtilis* Transition-Phase, Spore-Associated Antibacterial Protein TasA", Journal of Bacteriology, vol. 181, No. 17, Oct. 1999, pp. 5476-5481.

Tehri et al., "Biomarkers of bacterial spore germination", Annals of Microbiology, vol. 68, 2018, pp. 513-523.

Waller et al., "Ruthenium red staining for ultrastructural visualization of a glycoprotein layer surrounding the spore of *Bacillus anthracis* and *Bacillus subtilis*", Journal of Microbiological Methods, vol. 58, 2004, pp. 23-30.

Wang et al., "Kinetics of Germination of Wet-Heat-Treated Individual Spores of *Bacillus* Species, Monitored by Raman Spectroscopy and Differential Interference Contrast Microscopy", Applied and Environmental Microbiology, vol. 77, No. 10,m May 2011, pp. 3368-3379.

Wilson et al., "Bio-production of gaseous alkenes: ethylene, isoprene, isobutene", Biotechnology for Biofuels, vol. 11, 2018, 11 pages.

Yu et al., "Identification of volatile compounds released by myxobacteria *Sorangium cellulosum* ABH103-1", African Journal of Microbiology Research, vol. 5, Feb. 11, 2011, pp. 353-358.

* cited by examiner

Manufacturer A *G. stearothermophilus* Spores in 10x Diluted (DF) Manufacturer C growth medium Manufacturer A *G. stearothermophilus* Spores in 10x diluted (DF) Manufacturer C growth medium (second study)

METHOD TO VERIFY THE EFFECTIVENESS OF A STERILIZATION PROCESS BASED ON THE PRESENCE OF VOLATILE ORGANIC COMPOUNDS

RELATED APPLICATIONS

The present application claims priority to U.S. Provisional Patent Application No. 63/411,990, filed on Sep. 30, 2022, the entire contents of which are incorporated herein by reference.

FIELD OF THE INVENTION

The present invention relates generally to a method to verify the sterility assurance level of a sterilization process based on the presence of one or more volatile organic compounds as an indicator of spore germination.

BACKGROUND

Biological indicators are used to monitor whether the necessary conditions have been met to sterilize medical devices, instruments, and other products used where sterility is required. Bacterial spores possess the highest resistance to the various sterilization processes used today. Thus, most biological indicators (BI) used to monitor sterilization processes are made of bacterial endospores (spores). Since the mechanism of inactivation of the various sterilization processes may be different, different strains of bacteria have been selected to monitor the status of various sterilization processes. For instance, biological indicators for steam and oxidative sterilization processes typically include spores of *Geobacillus stearothermophilus* (formally known as *Bacillus stearothermophilus*), biological indicators for ethylene oxide processes typically include spores of *Bacillus atrophaeus* (formally known as *Bacillus subtilis*), and biological indicators for radiation processes typically include spores of *Bacillus pumilus*.

Understanding the revival process of a spore is critical to the development of the detection of surviving spores in order to determine if a sterilization process has failed. During dormancy, spores sense their environment, and when conditions are conducive to growth, they germinate. This happens upon the activation of a biological indicator where spores come into contact with a growth medium. The revival process is classically divided into two major phases, where the first phase is germination (germination and ripening stages), which is followed by the second phase, which is outgrowth. The passage from the spore back to a vegetative cell that can replicate itself may take up to two hours depending on the bacterial strain. Spore germination is triggered upon exposure to nutritional replenishment that occurs when the germinating molecules, including low-molecular-weight amino acids, sugars, and purine nucleosides, are sensed by germination receptors (GRs) located in the inner membrane of the spore. Because germination of individual spores in populations of all species is heterogeneous, some spores will take more time before committing to germination. In any event, the germination stage starts when the spore undergoes rehydration, followed by the release of dipicolinic acid (DPA) and partial core hydration. About 50% of spores will lose their resistance to heat and chemicals within 15 minutes of the start of the incubation process (activation), demonstrating that they went through the germination stage.

The germination stage is followed by the ripening stage that includes cortex hydrolysis, core hydration, core expansion, and loss of dormancy as well as more loss of resistance. During the first 20 to 40 minutes of spore germination, up to 20% of total dormant spore protein is degraded to free amino acids, of which 90% are small, non-enzymatic glycoproteins (SAPs) proteins. These are used in the synthesis of small molecules such as nucleotides and synthesis of new proteins. Proteins are being synthesized during germination without the need for external nutrients. At the end of the ripening stage, about 60 minutes after spore incubation (activation), the outgrowth phase starts. Outgrowth is the phase in which the spore activates the synthesis of macromolecules to become a vegetative cell and emerges from the disintegrating spore shell. Inhibition of the outgrowth phase is generally observed for spores exposed to sublethal concentration of a sterilizing agent (such as steam, $H_2O_2$, and EtO), but not the germination phase. Even spores exposed to high EtO concentrations can germinate freely under a variety of conditions but will not outgrow. Thus, detecting the germination of a spore is more sensitive then detecting its outgrowth and replication.

Detection of the presence of living spores after exposure to a sterilization process was first done based on their outgrowth to form a vegetative cell and subsequent multiplication of the vegetative cell. Then, in order to determine if a sterilization process was effective more quickly, new methods were developed to detect that dormant spores had entered the germination phase, indicating failure of the sterilization process being tested. However, these methods require the implementation fluorescence-based enzymatic assays and involve the addition of specific substrates, inducers, sources of biological activity (such as microorganisms including spores, enzymes, microbial metabolites, ATP, etc.), and/or spore modifications to incorporate the targeted enzymes (gene and/or protein), where the detection of an enzyme's activity only allows for detection of the spore germination indirectly. Such methods might lead to detection inaccuracy, additional steps, and other complications.

Therefore, there is a need for a method that can provide near real time, fast results without either spore modifications or the additional of potential germination inhibitors to directly determine if the spores in a biological indicator system have entered the germination phase, which is indicative of a failed sterilization process (e.g., steam, vaporized hydrogen peroxide, or ethylene oxide (EtO), ozone, $NO_2$, super critical $CO_2$, peracetic acid, or any other liquid or gas, or combination, meeting the requirement to be defined as a sterilizing agent).

SUMMARY OF THE INVENTION

Objects and advantages of the invention will be set forth in part in the following description, or may be obvious from the description, or may be learned through practice of the invention.

In one embodiment, the present invention is directed to a method for determining if a spore in a self-contained biological indicator is in a germination phase. The method includes subjecting a self-contained biological indicator to a sterilization process; exposing spores in the self-contained biological indicator to a growth medium; incubating the spores in the self-contained biological indicator; sampling headspace in the self-contained biological indicator; and determining if a volatile organic compound attributable to the germination phase of the spores in the biological indicator is released into headspace upon contact with the growth medium, wherein the presence of the volatile organic compound attributable to the germination phase of the spores in the self-contained biological indicator indicates failure of the sterilization process.

In one embodiment, determining if a volatile organic compound is released into headspace from the growth medium includes collecting an air sample from the headspace for volatile organic compound analysis.

In another embodiment, the sampling can occur within the self-contained biological indicator.

In still another embodiment, the sampling can occur outside the self-contained biological indicator.

In yet another embodiment, the air sample can be collected and analyzed in a time frame of less than about 60 minutes.

In an additional embodiment, the sterilization process can be a steam sterilization process.

In one more embodiment, the sterilization process can be a vaporized hydrogen peroxide sterilization process.

In another embodiment, the sterilization process can be an ethylene oxide sterilization process.

In still another embodiment, the self-contained biological indicator can include spores of *Geobacillus stearothermophilus* or *Bacillus atrophaeus*.

In yet another embodiment, the growth medium can include tryptic soy broth or modified soybean casein digest broth.

In an additional embodiment, the volatile organic compound can be polar.

In one more embodiment, the method can include applying a correction factor to remove any background volatile organic compounds attributable to the growth medium rather than the spores in the self-contained biological indicator in the germination phase.

In another embodiment, the volatile organic compound attributable to the germination phase of the self-contained biological indicator can include an alkane, an alcohol, an ester, a ketone, a furan, or a combination thereof. For example, the volatile organic compound attributable to the germination phase of the biological indicator can include 2-pentanone, methyl isobutyl ketone, 4-methyl-2-heptanone, 2-methyl-2-propanol, amylene hydrate, 3-hydroxy-2,4,4-trimethylpentyl 2-methylpropanoate, 2,2,4-Trimethyl-1,3-pentanediol diisobutyrate, 2-methyl-1,3-pentanediol, tetrahydro-2,2,5,5-tetramethyl-furan, or a combination thereof.

In one embodiment, the self-contained biological indicator can include a target level of spores to achieve a desired resistance in the self-contained-biological indicator depending on a type of sterilization process in which the self-contained biological indicator is utilized.

In still another embodiment, the presence of the volatile organic compound can be determined directly without the use of enzymatic reagents.

In yet another embodiment, the presence of the volatile organic compound can be determined directly without the use of a fluorescence moiety.

In an additional embodiment, determining if a volatile organic compound attributable to the germination phase of the spore in the biological indicator is released into headspace upon contact with the growth medium can include comparing a measured volatile organic compound level with a control volatile organic compound level for the growth medium.

In one more embodiment, it can be determined that a volatile organic compound attributable to the germination phase of the spore in the biological indicator is released into headspace upon contact with the growth medium if the measured volatile organic compound level is higher than the control volatile organic compound level.

In another embodiment, the present invention is directed to a method for determining sterilization success or failure. The method includes subjecting a self-contained biological indicator to a sterilization process; exposing spores in the self-contained biological indicator to a growth medium; incubating the spores in the self-contained biological indicator; sampling headspace in the self-contained biological indicator; and measuring a concentration level of a volatile organic compound released into headspace upon contact of the spores with the growth medium.

In one embodiment, measuring a concentration level of the volatile organic compound can include collecting an air sample from the headspace for volatile organic compound analysis.

In another embodiment, the sampling can occur within the self-contained biological indicator.

In yet another embodiment, the sampling can occur outside the self-contained biological indicator.

In still another embodiment, the air sample can be collected for and analyzed in a time frame of less than about 60 minutes.

In an additional embodiment, an increase in the concentration of the volatile organic compound compared to a baseline level can indicate success of the sterilization process.

In one more embodiment, the sterilization process can be a steam sterilization process, a vaporized hydrogen peroxide sterilization process, or an ethylene oxide sterilization process.

In another embodiment, the self-contained biological indicator can include spores of *Geobacillus stearothermophilus* or *Bacillus atrophaeus*.

In still another embodiment, the growth medium can include tryptic soy broth or modified soybean casein digest broth.

In yet another embodiment, the volatile organic compound can be non-polar.

In another embodiment, the volatile organic compound can include cyclododecanol; benzoic acid, 4-ethoxy-, ethyl ester; 3,4,4-trimethyl-3-pentanol; or a combination thereof.

In an additional embodiment, the presence of the volatile organic compound can be determined directly without the use of enzymatic reagents.

In yet another embodiment, the presence of the volatile organic compound can be determined directly without the use of a fluorescence moiety.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1A:
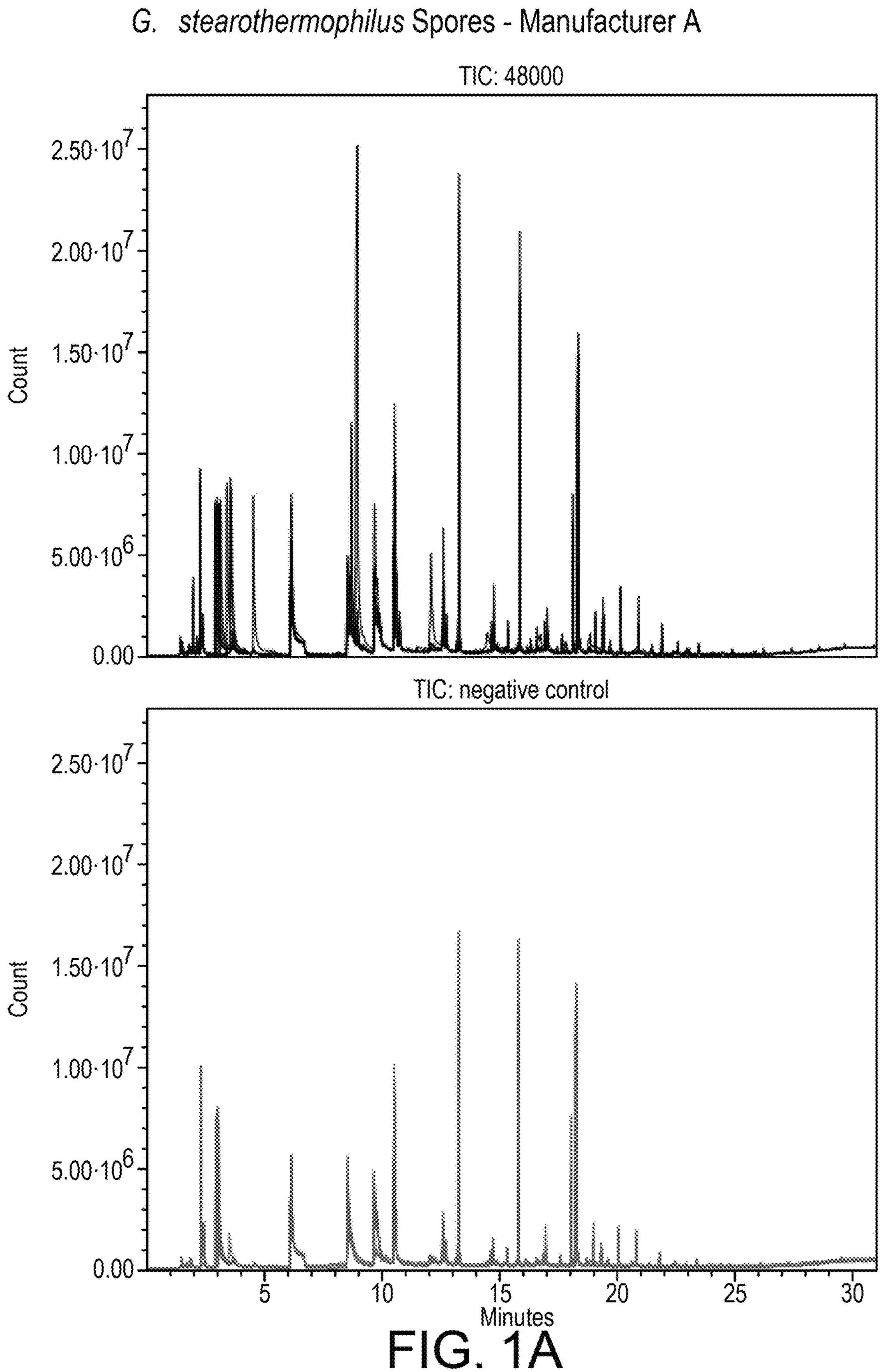
FIG. 1A illustrates two total ion chromatograms (TICs) used to study the headspace volatile organic compounds released from a cell count of 48,000 viable spores of *G. stearothermophilus* from Manufacturer A in a 10× diluted soybean casein digest broth growth medium (top graph) and a negative control of a cell count of 48,000 steam sterilized *G. stearothermophilus* spores in the same 10× diluted growth medium (bottom graph) over a time period of 20 minutes of incubation/germination at 60° C.
Figure 1B:
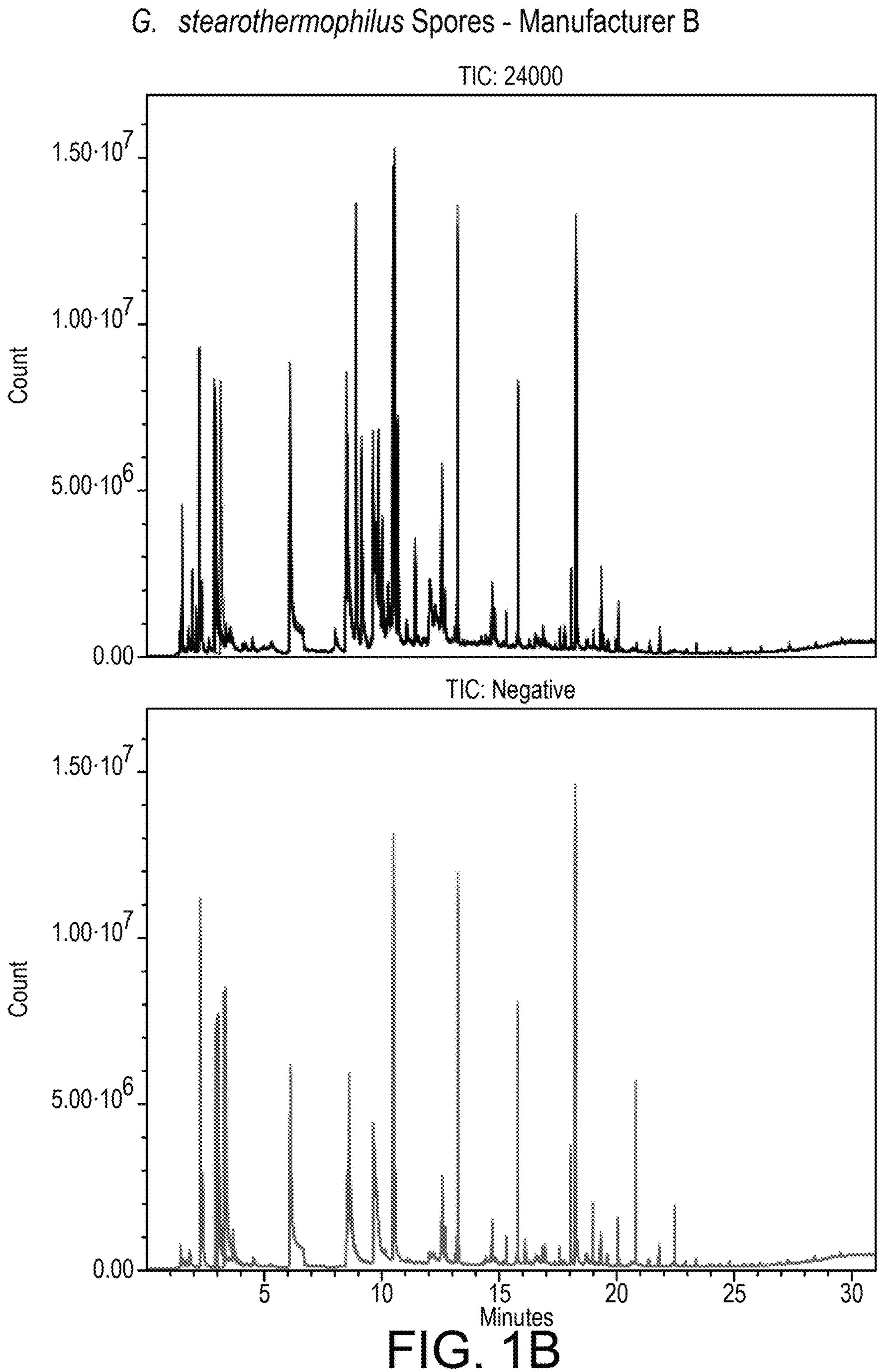
FIG. 1B illustrates two total ion chromatograms (TICs) used to study the headspace volatile organic compounds released from a cell count of 24,000 spores of *G. stearothermophilus* from Manufacturer B in a 10× diluted soybean casein digest broth growth medium (top graph) and a negative control of a cell count of 24,000 steam sterilized spores from of *G. stearothermophilus from Manufacturer B in a* 10× diluted soybean casein digest broth growth medium (bottom graph) over a time period of 20 minutes incubation/germination at 60° C.
Figure 2A:
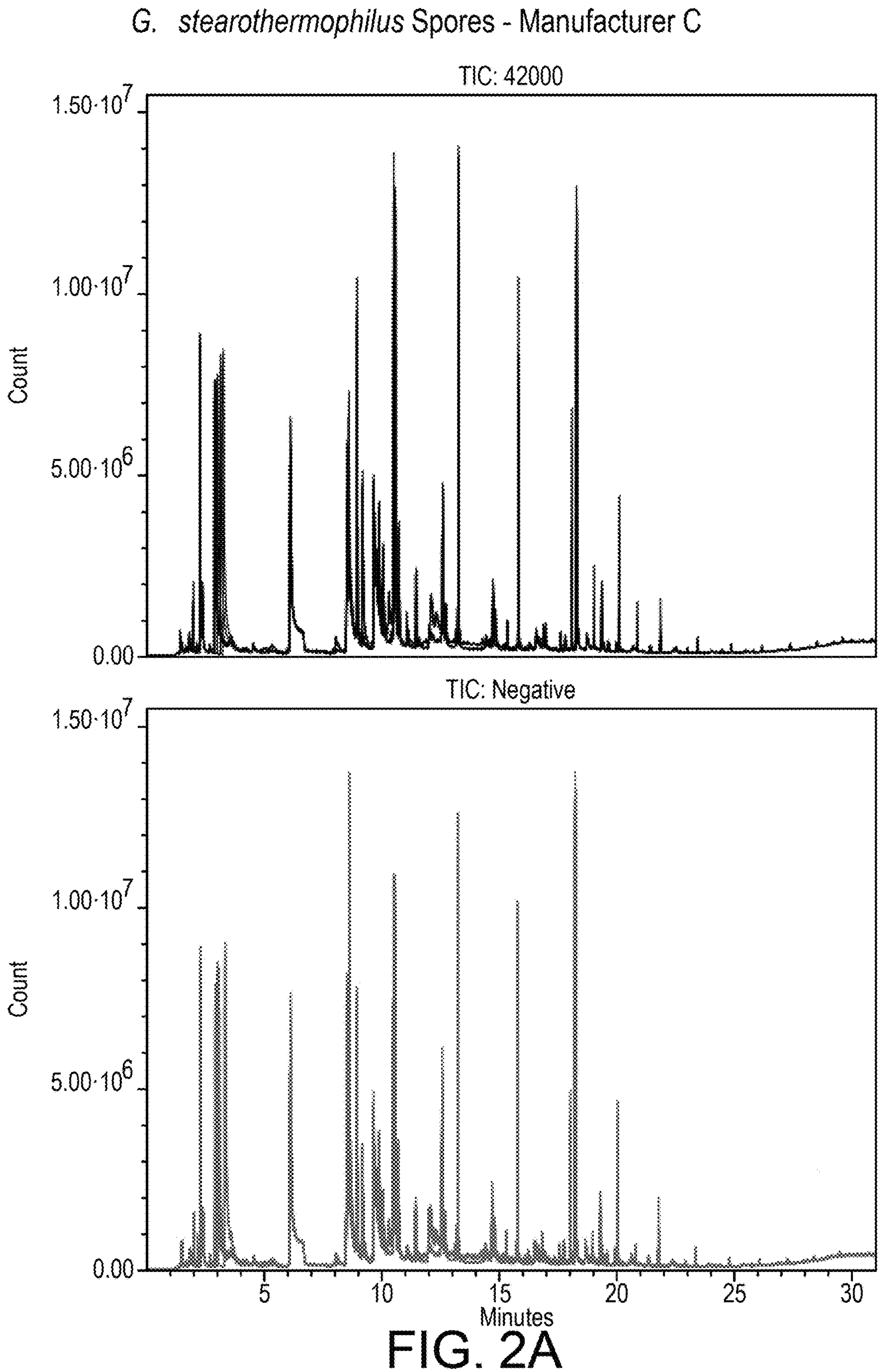
FIG. 2A illustrates two total ion chromatograms (TICs) used to study the headspace volatile organic compounds (VOCs) released from a cell count of 42,000 spores of *G. stearothermophilus* from Manufacturer C in a 10× diluted soybean casein digest broth growth medium (top graph) and a negative control of a cell count of 42,000 steam sterilized spores from of *G. stearothermophilus* from Manufacturer C in a 10× diluted soybean casein digest broth growth medium (bottom graph) over a time period of 20 minutes of incubation/germination at 60° C.
Figure 2B:
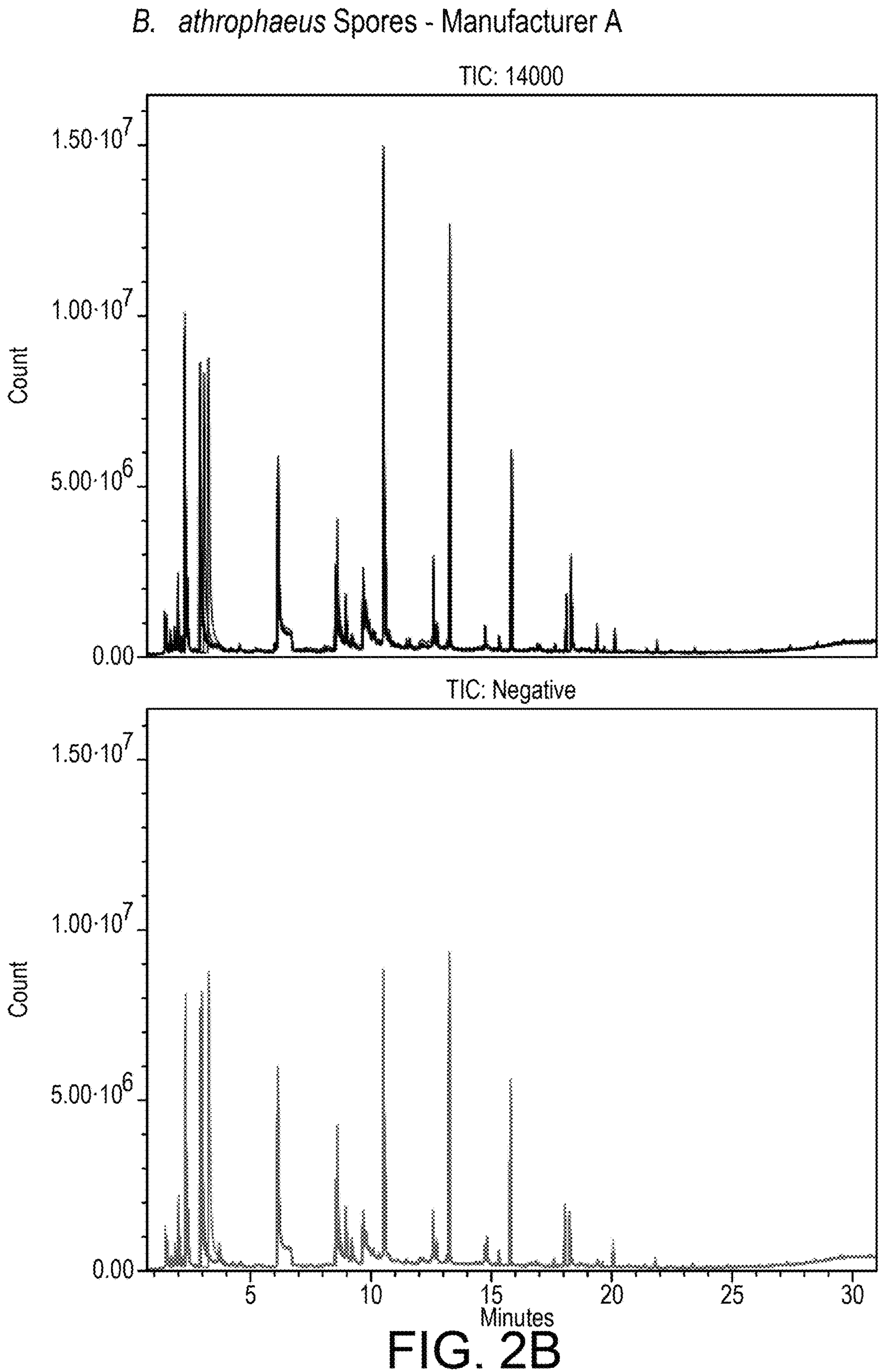
FIG. 2B illustrates two total ion chromatograms (TICs) used to study the headspace volatile organic compounds released from a cell count of 14,000 spores from of *B. atrophaeus* from Manufacturer A in a 10× diluted soybean casein digest broth growth medium (top graph) and a negative control of a cell count of 14,000 ethylene oxide sterilized spores from of *B. atrophaeus* from Manufacturer A in a 10× diluted soybean casein digest broth growth medium (bottom graph) over a time period of 20 minutes incubation/germination at 37° C.

Reference will now be made in detail to one or more embodiments of the invention, examples of the invention, examples of which are illustrated in the drawings. Each example and embodiment is provided by way of explanation of the invention and is not meant as a limitation of the invention. For example, features illustrated or described as part of one embodiment may be used with another embodiment to yield still a further embodiment. It is intended that the invention include these and other modifications and variations as coming within the scope and spirit of the invention.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a method for determining if a spore in a self-contained biological indicator is in a germination phase, even when a very low concentration of spores are activated and proceed to outgrowth phase. The method includes subjecting a self-contained biological indicator to a sterilization process; exposing spores in the self-contained biological indicator to a growth medium; incubating the spores in the self-contained biological indicator; sampling headspace in the self-contained biological indicator; and determining if a volatile organic compound attributable to the germination phase of spores in the self-contained biological indicator is released into headspace upon contact with the growth medium. The presence of the volatile organic compound attributable to the germination phase of the spores in the self-contained biological indicator indicates failure of the sterilization process. The sterilization process can utilize steam, vaporized hydrogen peroxide, or ethylene oxide ozone, $NO_2$, super critical $CO_2$, peracetic acid, or any other liquid or gas, or combination, meeting the requirement to be defined as a sterilizing agent, and the biological indicator is present during the sterilization process, after which the biological indicator is introduced into a growth medium and an air sample above the growth medium can be collected and analyzed for the presence of certain volatile organic compounds (VOCs) to verify or determine if the sterilization process was successful, as certain VOCs can be attributable to and released into the headspace by spores that are in the germination phase, which means they are active and have not been killed during the sterilization process.

In another embodiment, the present invention is directed to a method for determining sterilization success. The method includes subjecting a self-contained biological indicator to a sterilization process; exposing spores in the self-contained biological indicator to a growth medium; incubating the spores in the self-contained biological indicator; sampling headspace in the self-contained biological indicator; and measuring a concentration level of a volatile organic compound released into headspace upon contact of the spores with the growth medium. The presence of the volatile organic compound in the self-contained biological indicator can indicate success of the sterilization process. The sterilization process can utilize steam, vaporized hydrogen peroxide, or ethylene oxide ozone, $NO_2$, super critical $CO_2$, peracetic acid, or any other liquid or gas, or combination, meeting the requirement to be defined as a sterilizing agent, and the biological indicator is present during the sterilization process, after which the biological indicator is introduced into a growth medium and an air sample above the growth medium can be collected and analyzed for the presence of certain volatile organic compounds (VOCs) to verify or determine if the sterilization process was successful, as certain VOCs can be attributable to and released into the headspace by the growth medium and can increase in level after sterilization.

The present inventors have found that the methods of the present invention can improve the detection of the growth phase or biological activity for highly resistant microorganisms (e.g., endospores or bacterial spores such as, but not limited to, *Bacillus atrophaeus,* and *Geobacillus stearothermophilus* (*Bacillus Bacillus stearothermophilus, Bacillus megaterium, Bacillus coagulans, Clostridium sporogenes, Bacillus pumilus,* or combinations thereof) by focusing on volatile organic compound (VOC) detection and measurement, where specific VOCs are quickly found in the headspace of a container that includes a biological indicator containing spores and a growth medium after a sterilization cycle is or is not successful. For instance, in some instances, the presence of a particular level of VOC can indicate failure of a sterilization process or cycle, while in other instances, an increase over time of a particular VOC level can indicate success of the sterilization process or cycle. The time for detecting and reporting of the growth or biological activity can be shortened to less than about 30 minutes, such as less than about 15 minutes. This time frame is much quicker than many current methods that require culturing growth medium for turbidity, which can take as long as 2-7 days to verify that a sterilization cycle was successful when there is a lack of turbidity. Further, no fluorescence moieties or measurements are required, which can take longer and involve additional complications and room for error due to the use of enzymatic substrates, spore modifications, etc. In other words, the presence of volatile organic compounds can be determined directly without extra steps and reagents.

The biological indicator can include spores of *Geobacillus stearothermophilus* or *Bacillus atrophaeus,* although other spores are also contemplated by the present invention. Further, the number of spores present as part of the biological indicator can be at least 100,000 spores for steam sterilization methods and at least 1,000,000 spores for ethylene oxide and hydrogen peroxide sterilization methods.

Meanwhile, the growth medium into which the biological indicator is introduced in order to determine if the spores enter the germination phase to indicate failure of the sterilization process being validated or analyzed can be any suitable growth medium, including, but not limited to, tryptic soy broth or modified soybean casein digest broth (e.g., Manufacturers A, B, C, D, and E). In some embodiments, the growth medium can be diluted (e.g., dilute 1, 2, or 10 times) in order to minimize the effect of background VOCs that may be present in the growth medium.

Once the biological indicator is introduced to the growth medium, heat can be applied to the growth medium/biological indicator combination at a temperature ranging from about 50° C. to about 65° C., such as from about 55° C. to about 60° C., for steam and hydrogen peroxide sterilization. Meanwhile, heat can be applied at a temperature ranging from about 25° C. to about 40° C., such as from about 30° C. to about 35° C., such as from for ethylene oxide sterilization.

Once the biological indicator is in contact with the growth medium (activated), the biological indicator is incubated at the temperature range optimum for its germination, such as from about 50° C. to about 65° C. for *G. stearothermophilus* spores and from about 25° C. to about 40° C. for *B. atrophaeus* spores. The heat can be applied for a time frame of less than about 60 minutes, such as less than about 20 minutes, such as a time frame ranging from about 1 minute to about 20 minutes, such as from about 3 minutes to about 17 minutes, such as from about 5 minutes to about 15 minutes, during which time an air sample of the headspace above the growth medium can be collected for VOC analysis. The headspace can be collected onto any suitable sampling platform during this time, such as an adsorbent film that can trigger a measurable electrical signal (e.g., in order to then measure resistance level changes), a fiber for carrying out a solid-phase microextraction/gas chromatography-mass spectrometry (SPME/GC-MS) method, etc. Then, it can be determined if a VOC is attributable to the germination phase of the biological indicator, signaling a failed sterilization cycle, by comparing the measured level of a particular VOC with a control VOC level for the growth medium alone, absent any spores and/or absent any active spores. For instance, it can be determined that a VOC attributable to the germination phase of the biological indicator is released into headspace from the growth medium if the measured VOC level is higher than the control VOC level. In addition to including a level of VOCs associated with the growth medium, it should be understand that the control VOC level can also include VOCs attributable to other non-spore components of the biological indicator, such as, but not limited to, a cap, filter, sleeve, spore carrier, VOC measurement board, etc.

Particular VOCs that can be identified by the methods of the present invention that are indicative of an unsuccessful sterilization cycle due to the presence of spores in growth medium can be polar in nature and can include ketones, alcohols, esters, and furans. In particular, the VOCs that can be detected in the presence of spores regardless of the type of growth medium utilized can include 2-pentanone, methyl isobutyl ketone, and 4-methyl-2-heptanone in the ketone family; 2-methyl-2-propanol, amylene hydrate, and 2-methyl-1,3-pentanediol in the alcohol family; 3-hydroxy-2,4,4-trimethylpentyl 2-methylpropanoate and 2,2,4-Trimethyl-1,3-pentanediol diisobutyrate in the ester family; and tetrahydro-2,2,5,5-tetramethyl-furan in the furan family. Further, it is to be understood that the methods of the present invention can utilize a correction factor in the form of an algorithm to subtract out baseline VOC levels that may be emitted by the growth medium to differentiate between VOCs that may be released by the spores during germination and those that are present in the growth medium alone.

The present invention may be better understood by reference to the following example.

EXAMPLE

Materials

Manufacturer A, B, C, D and E Growth Media

SPME fiber: A solid-phase micro-extraction (SPME) fiber coated with 50/30 μm divinylbenzene/carboxen (DVB/CAR)/PDMS (Sigma-Aldrich, catalog number 57348-U) was used for headspace VOC extraction.

Three commercially available biological indicator (BI) products for steam-based sterilization along with two BIs for ethylene oxide-based sterilization and one BI for hydrogen peroxide-based sterilization were obtained: Manufacturer A, B and C spore suspensions as self-contained biological indicators VOC standards and HPLC water: All VOC standards and HPLC grade water were obtained from Sigma Aldrich. They were directly used without further treatment.

Sample Preparation

Stock spore suspensions were prepared by suspending the targeted spores in the HPLC water. Depending on the form factors of BI products, it could be done by either suspending the BI carriers in HPLC water or adding HPLC water into the BI container to remove the attached spores. The spore suspensions prepared from BIs for steam sterilization and vapor hydrogen peroxide were heat shocked for 15 minutes at 95° C. The 15 minutes began when the liquid reached 85° C. Ethylene oxide spore suspensions were heat shocked at 80° C. for 10 minutes, 10 minutes started once solution reached 70° C. After heat shock, the mixture was allowed to cool to room temperature. The cooled mixture was then serially diluted six times in ten-fold steps. Each dilution was plated in 20 uL triplicates on TSA plates to confirm target concentration of spore spiking. The plates were incubated at 60° C. or 37° C. (depending on the types of spores) for 24 hours before obtaining plate counts. All dilutions were labeled with proper concentrations and stored at 4° C. until use. All spore suspensions used for GCMS analysis were examined to confirm the number of spores in the GC/MS sample.

To establish a baseline of VOCs from treated BIs, each spore type was sterilized according to manufacturer's protocol where the sterilized spores were then recovered in HPLC water. For baseline studies, treated spores (plated to confirm death/lack of growth) were inoculated into growth medium. This allowed to identification of new VOCs from untreated spores (plated to confirm cell concentrations) within the 15 minutes germination window. A study was also conducted to determine if BIs sterilized for one or two cycles provided differing VOCs.

All GCMS spores samples were prepared in a gas-tight 10 ml glass vial containing 500 uL to 1 ml of growth media. Vials were real-time spiked with 40 to 50 ul of spore suspensions 2-3 minutes before the start of the 15-minute incubation/fiber VOC collection began. Inoculated sample spore concentrations targeted two ranges: low (100-900 spores per vial) and high (10,000-90,000 spores per vials). Spore suspension concentrations were confirmed after heat-shock treatment and again when running samples. Spore suspensions were spread over TSA plates in triplicate and incubated at 60° C. or 37° C. for 24 hours depending on spore type.

Headspace VOC

Headspace VOC analysis was carried out with SPME/GC-MS using an Agilent 8890 GC, paired with Agilent 7250

Q-TOF 7250 Q-TOF (Agilent, Santa Clara, CA) system equipped with a Gerstel TDU/CIS autosampler (Gerstel GmbH & Co., Germany). The instrument was coupled with a sample preparation system (Gerstel GmbH & Co., Germany) for incubation and sample agitation. The SPME fiber was inserted into the headspace of the sample vial at the beginning of incubation. The sample vial was agitated either at 60° C. or 37° C. for VOC extraction. All fibers were conditioned in the GC injection port before use, as directed by manufacturers' guidelines.

The fiber collected VOCs from the headspace for 15 minutes and desorbed them into the GC injector for 3 minutes at 250° C. The chromatographic separation was performed via a DB-5 GC column (L×I.D. 30 m×0.25 mm, film thickness 0.25 μm, Agilent Technologies, Palo Alto, CA, USA). The GC oven temperature was programmed to increase from 40 to 280 C at 10 C/min. Helium served as the carrier gas with a constant column flow rate of 1.2 ml/min. The transfer line temperature was maintained constant at 220° C. Upon exiting the column, compounds were ionized via electron impact at 70 eV and detected with a time-of-flight mass spectrometer with a mass/charge ratio (m/z) ranging from 45 to 300 Thomson. The mass/charge ratio was selected to avoid the background from $N_2$ and $CO_2$. The data were processed using the Agilent MassHunter Unknowns Analysis Version10.0 software using the SureMass algorithm and NIST17 EI library search to identify additional potential compounds of interest in headspace VOC. Agilent Mass Profiler Professional (MPP) Version 15.1 software was used to compare and extract the VOCs with significant difference among different groups. MPP was also used to conduct statistical analysis including ANOVA, PCA, fold analysis, volcano plots, hierarchical trees, SOMs, and multiple methods for class prediction.

Results

SPME-GC-MS for Microbial VOC Study

Monitoring of volatile emissions of bacteria has been facilitated by use of SPME-GC-MS. SPME is an extraction method that combines sampling, extraction, and concentration of analytes. SPME based headspace VOCs extraction is a passive sampling approach that does not interfere with the sample. Additionally, this method provides the benefit of automation with increased sensitivity and consistency. The polarity of the adsorbent ranging from non-polar PDMS to polar polyacrylate coating on the fiber can be tailored based on the application. PDMS/DVB/CAR fiber with medium polarity was selected due to the facts that VOCs with diverse polarities are produced from microorganisms and this type of fiber was reported to extract a wider range of microbial VOCs, including low molecular weight compounds, which is an intrinsic property of this fiber type.

Spore VOC During Germination

Spore suspensions with BIs for steam sterilization obtained from Manufacturer A, B, and C, ethylene oxide (ETO) obtained from Manufacturer A and vapor hydrogen peroxide (VHP) obtained from Manufacturer A and B were prepared. To examine the emissions of spore-VOCs during germination, heat activated spore suspensions were incubated at their optimum temperatures (60° C. for steam and vaporized hydrogen peroxide BI, 37° C. for ETO BI) while headspace VOC were collected for 15 minutes using a SPME fiber. Spore suspensions were heat activated so the rate and extent of germination of spores are increased. The headspace VOC collection was limited to 15 minutes as the spore germination typically takes place from 0 to 15 minutes. After 15 minutes headspace VOC extraction, the SPME fiber was heated at 250° C. for 3 min at the GC inlet to desorb the attached VOCs. The desorbed VOCs were flowed into the GC column by a carrier gas at a rate of 1.2 ml/min. Detailed GC/MS data collection and analysis can be found in the Experimental section.

For this study, 1 ml of 10-fold Manufacturer C diluted media inside a 10 ml of glass vial was spiked with 40 μl of heat-activated spore suspensions with known concentrations. The confirmed high range spore counts averaged 48,000, 24,000, 42,000 and 14,000 per sample vial for Manufacturer A (steam), Manufacturer B (steam), Manufacturer C (steam) and Manufacturer A (ethylene oxide) respectively, and the confirmed low range spore counts averaged 100 times lower than the corresponding high range spore counts. Negative control samples were prepared in a same way with spiking of sterilized spore suspensions with the high range spore counts. The total ion chromatograms (TIC) of backgrounds (negative control) and viable spore-containing (positive) samples can be found in FIGS. 1A-1B and FIGS. 2A-2B.

It can be seen that the number of peaks and peak intensities are much higher in the TICs collected the positive samples compared to negative controls. To extract the VOCs from the TIC, SureMass algorithm was applied and features were extracted by spectral deconvolution. The number of extracted features from positive and negative spore samples can be found in Table 1. The number of features in negative samples are around 180 and the number of features for positive samples are highly dependent on the type of BIs.

MPP was conducted to compare the features obtained from positive and negative samples. Two selection criteria were used to extract VOCs released from spores: (a) the peak intensity in the spore-containing sample is at least 2-fold difference (either increase or reduced intensity) compared to negative; (b) this compound is present in above 80% of positive samples. Based on these selection criteria, the number of VOCs associated with viable spores can be found in Table 1.

Figure 3:
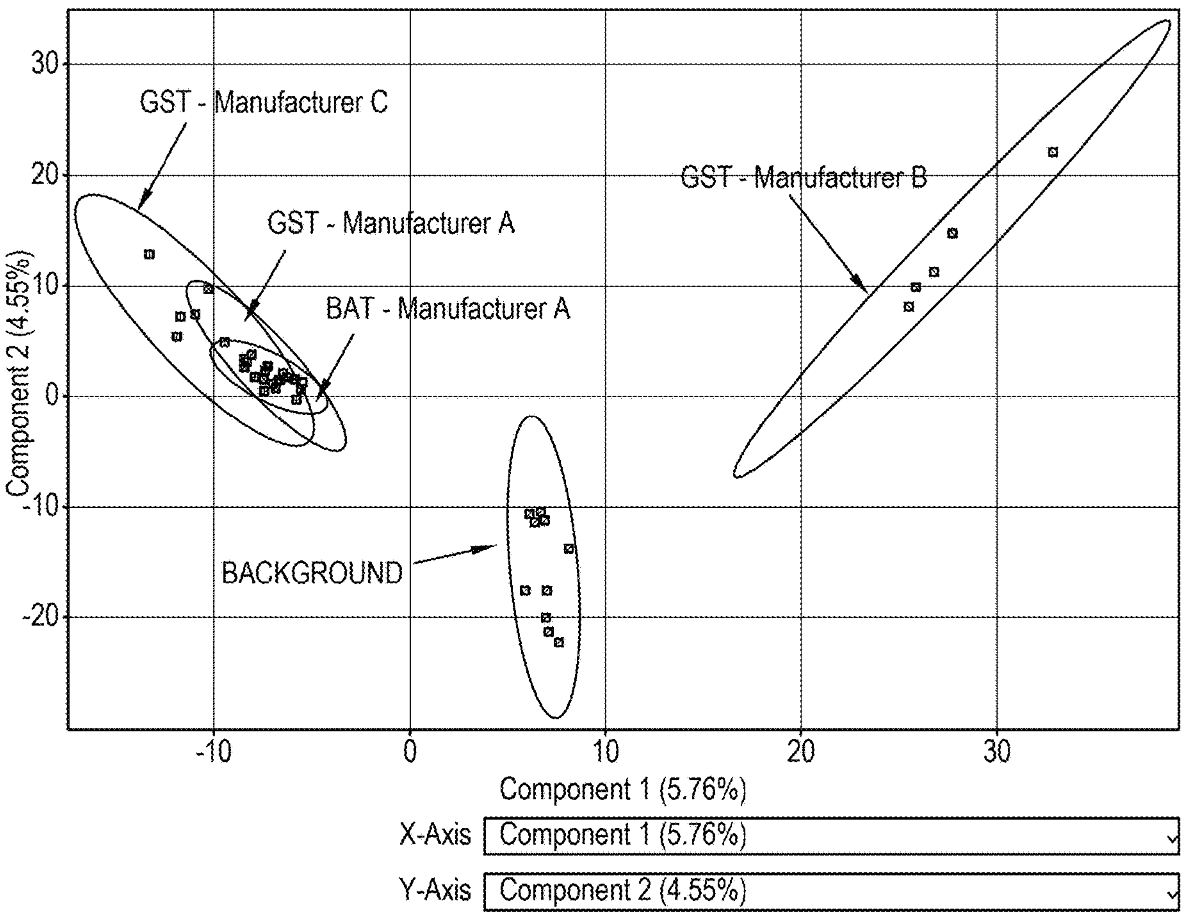
FIG. 3 illustrates the difference in headspace VOC signatures in the various types of biological indicator spore suspensions and in the background growth medium, as shown via principal component analysis (PCA)

Some of the common putative spore VOCs include 2-methyl-2-propanol, acetic acid, pentyl ester, amylene hydrate, methyl isobutyl ketone, tetrahydro-2,2,5,5-tetramethyl-furan, etc. Our initial VOC results clearly indicate the emissions of spore VOC during germination. Based on the VOC signatures, we are able to distinguish the viable BIs from the sterilized sample and differentiate the type of BIs implemented in the sterilization process, as demonstrated in the PCA analysis shown in FIG. 3.

TABLE 1

Number of features identified from high range spore samples

| Type of Spore | Cell Counts | Positive Sample | Negative Sample | Spore-VOC |
|---|---|---|---|---|
| Manufacturer A Steam | 48,000 | 238 ± 33 | 190 ± 12 | 24 |
| Manufacturer B Steam | 24,000 | 305 ± 19 | 189 ± 14 | 53 |
| Manufacturer C Steam | 42,000 | 255 ± 26 | 225 ± 13 | 26 |
| Manufacturer A Ethylene Oxide | 14,000 | 182 ± 11 | 175 ± 6 | 21 |

Impact of Growth Medium and Cell Counts

Growth medium has an important role in volatile production and function by influencing metabolism and the growth rate. Growth medium itself emits significant background VOCs including pyrazine VOCs, byproducts of the sterilization of growth media through autoclaving heats amino acids and reducing sugars. Background VOC profiles from different growth media including Manufacturer A, C, D and E were examined. In this study, a volume of 500 ul of growth media were placed inside a 10 ml glass vial and followed the same VOC extraction method for headspace VOC analysis.

Figure 4:
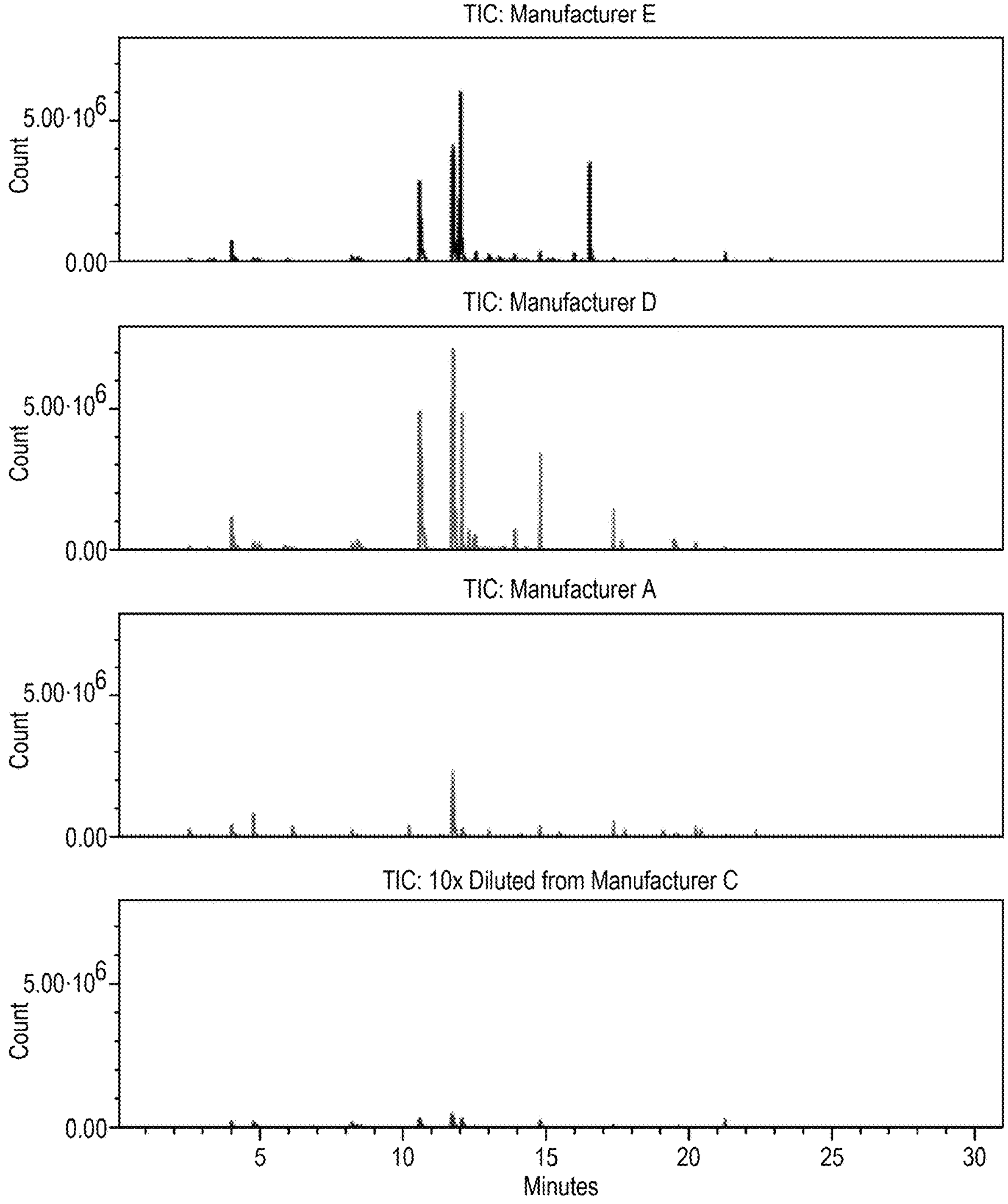
FIG. 4 illustrates four total ion chromatograms (TICs) collected from headspace VOCs from Manufacturer E growth medium, Manufacturer D growth medium, Manufacturer A growth medium, and 10× diluted (DF) Manufacturer C growth medium, which are all modified tryptic soy broth mediums.
Figure 5:
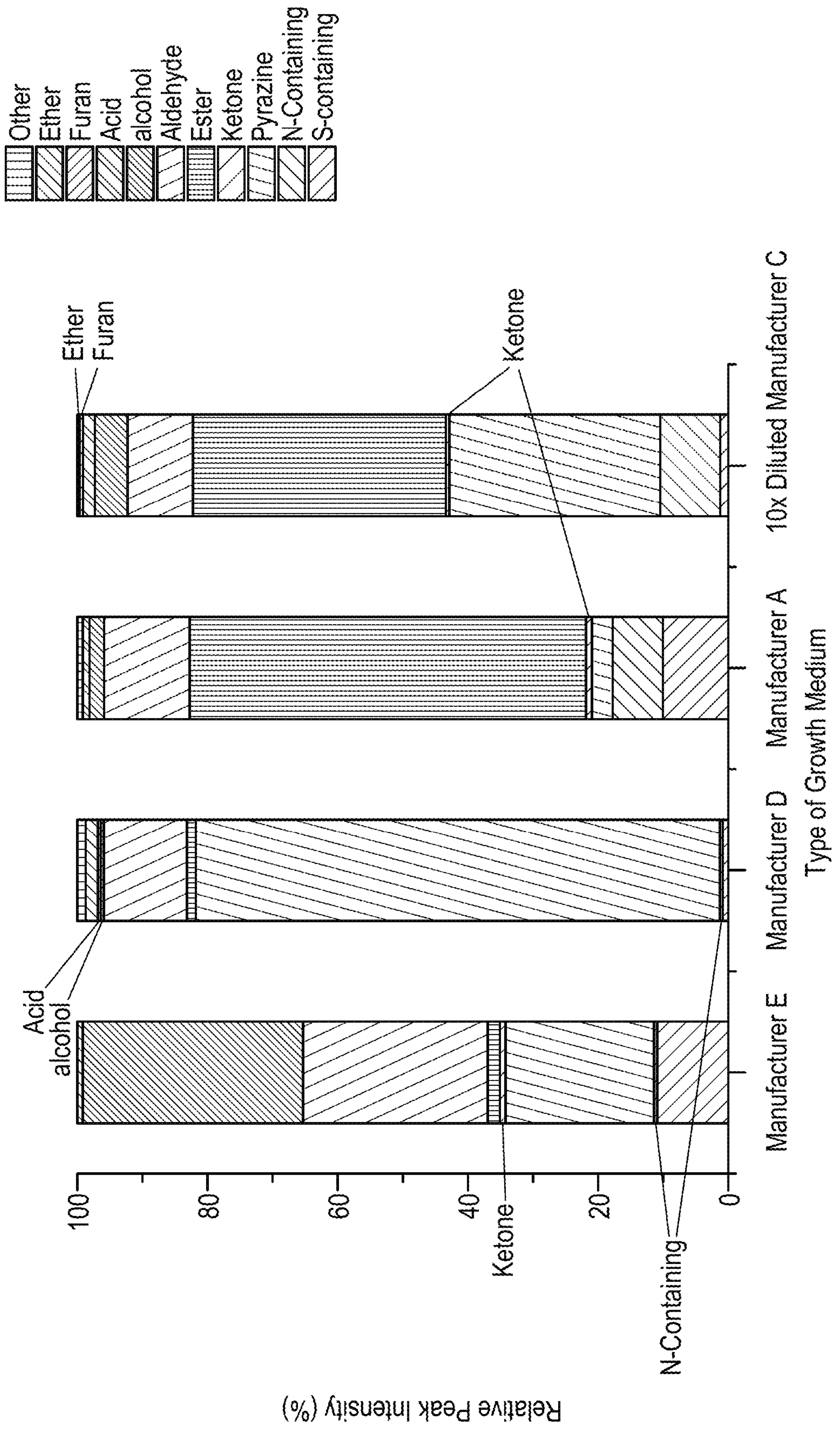
FIG. 5 is a graph illustrating the relative peak intensities from different groups of VOCs emitted from the various spore growth media from FIG. 4.

The number of background VOCs can be found in Table 2 and their corresponding TICs can be found in FIG. 4. It can be clearly seen that both peak intensities and number of peaks are greater in Manufacturer D and E growth medium compared to Manufacturer A medium and Manufacturer C 10-fold diluted medium. It was observed that the Manufacturer A and E growth medium contains higher level of S-containing compounds, as shown in FIG. 5. The growth medium obtained from Manufacturer D contains very high relative level of pyrazine related compounds. Both Manufacturers A and C growth medium contain increased relative level of ester and N-containing compounds compared to Manufacturers D and E.

To minimize the background interference, Manufacturer C 10-fold diluted medium was selected for later spore VOC studies. The rates of spore germination and growth in both Manufacturer C 10-fold diluted and manufacturer A media were compared and confirmed using both Manufacturer A spores for ethylene oxide and steam-based sterilization.

TABLE 2

Background VOCs identified from different growth media

| Growth Medium | Number of VOCs Identified |
|---|---|
| Manufacturer E | 239 ± 8 |
| Manufacturer D | 232 ± 8 |
| Manufacturer A | 180 ± 17 |
| Manufacturer C 10× df | 126 ± 7 |

Figure 6:
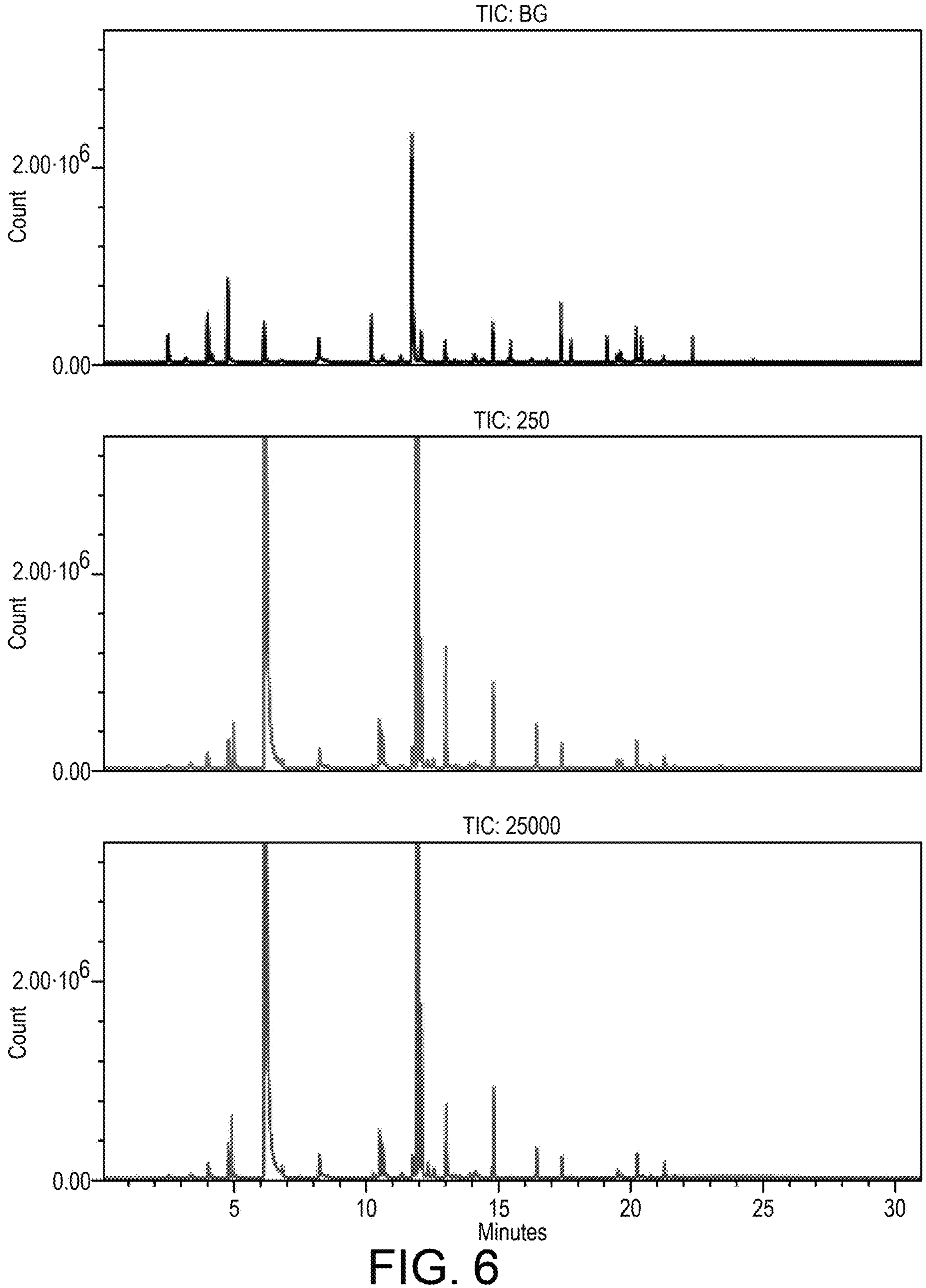
FIG. 6 illustrates three total ion chromatograms (TICs) collected from headspace VOCs from Manufacturer A medium (background), 250 *G. stearothermophilus* spores in Manufacturer A growth medium, and 25,000 *G. stearothermophilus* spores in Manufacturer A growth medium.
Figure 7:
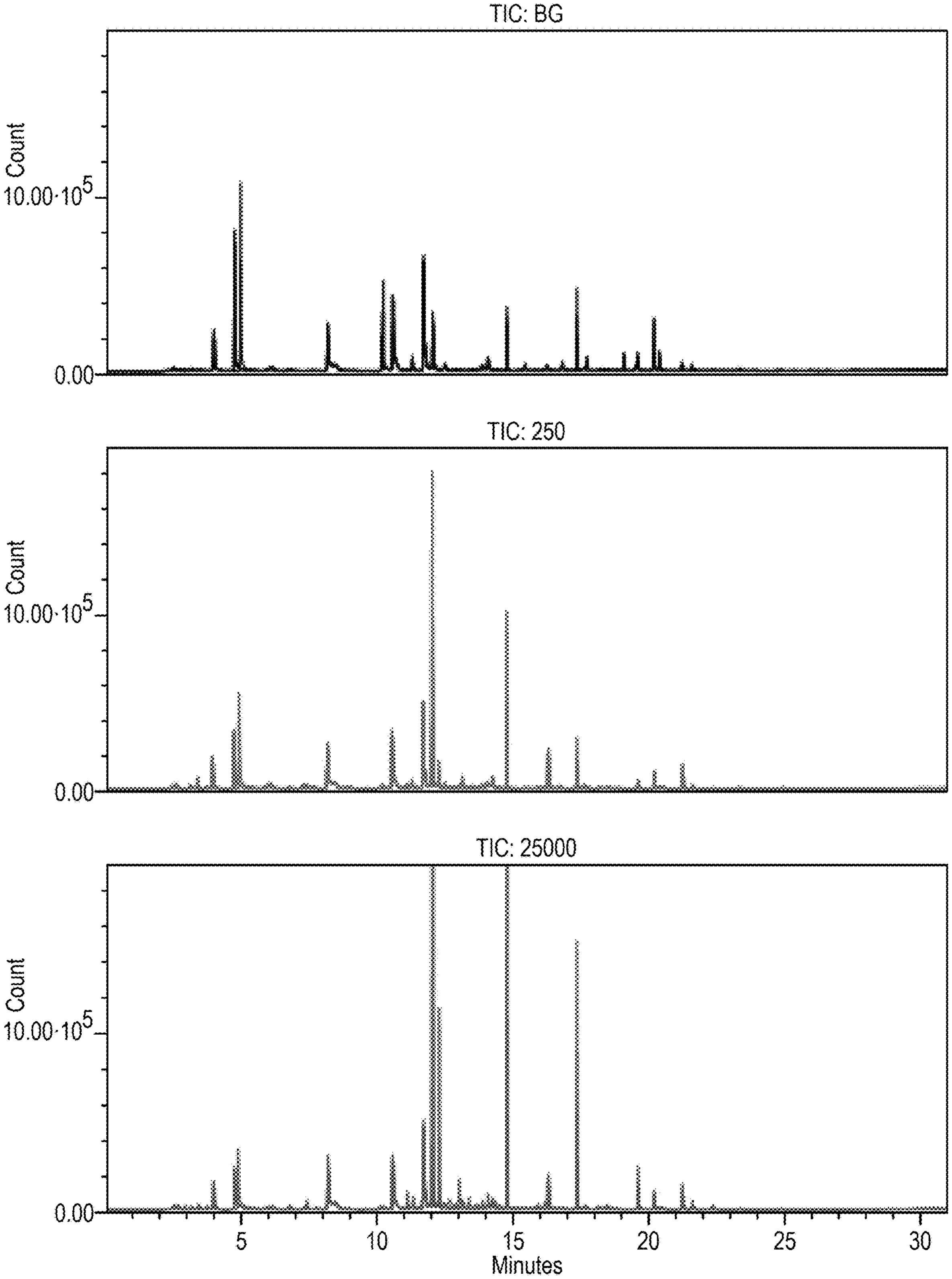
FIG. 7 illustrates three total ion chromatograms (TICs) collected from headspace VOCs from 10× diluted (DF) Manufacturer C growth medium (background), 250 *G. stearothermophilus* spores in 10× diluted (DF) Manufacturer C growth medium, and 25,000 *G. stearothermophilus* spores in 10× diluted (DF) Manufacturer C growth medium.
Figure 8A:
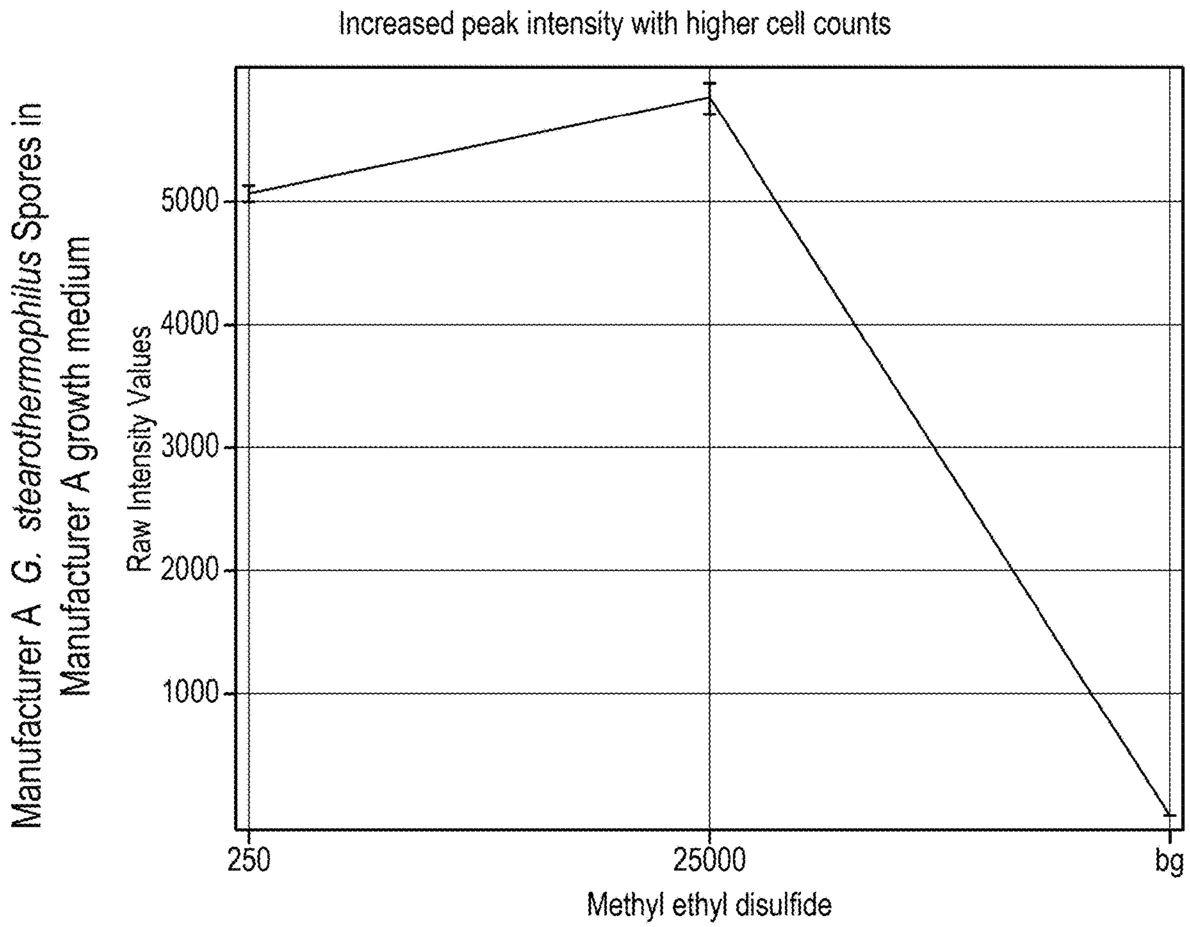
FIG. 8A illustrates the peak intensity by spore cell count of the VOC methyl ethyl disulfide when Manufacturer A *G. stearothermophilus* spores were in manufacturer A growth medium.
Figure 8B:
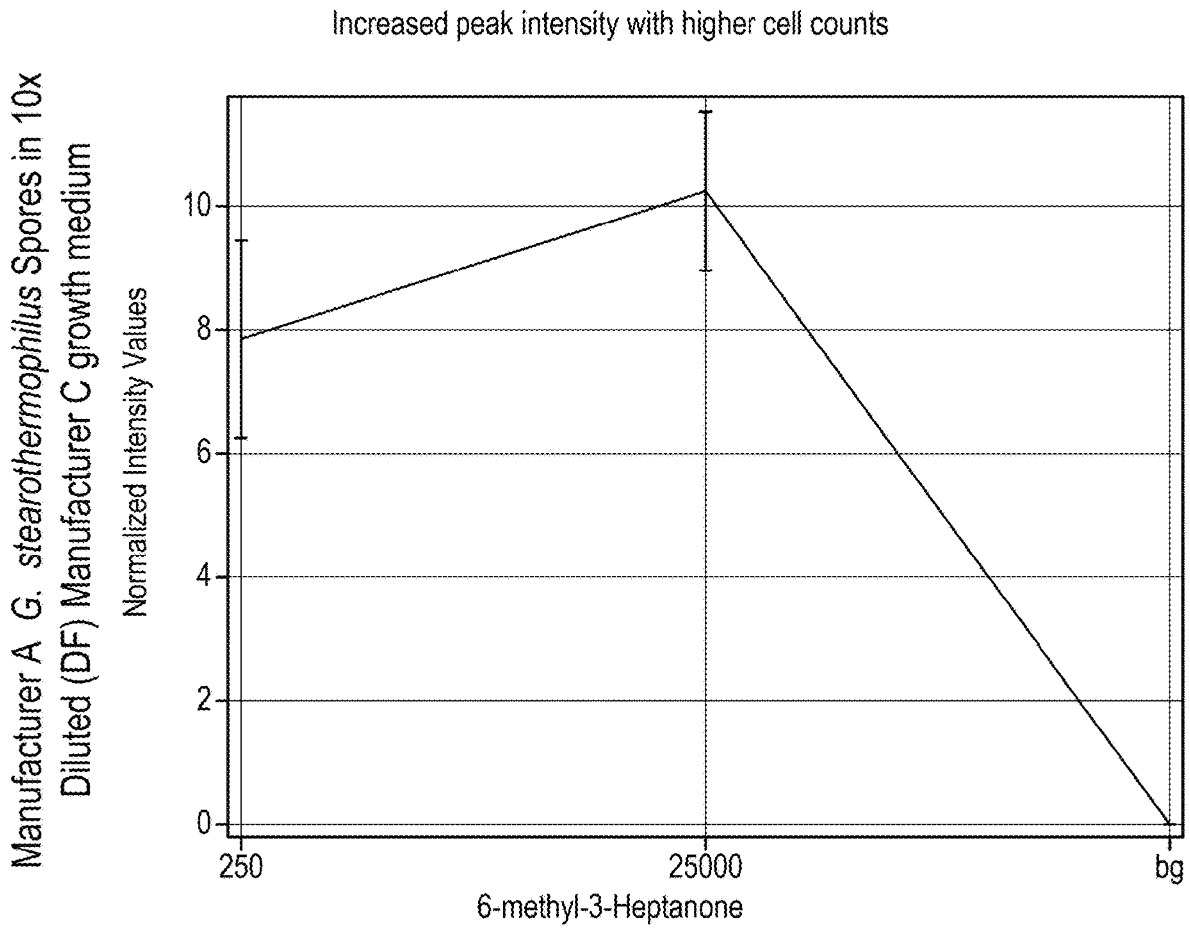
FIG. 8B illustrates the peak intensity by spore cell count of the VOC 6-methyl-3-heptanone when Manufacturer A *G. stearothermophilus* spores were in 10× diluted (DF) Manufacturer C growth medium.
Figure 8C:
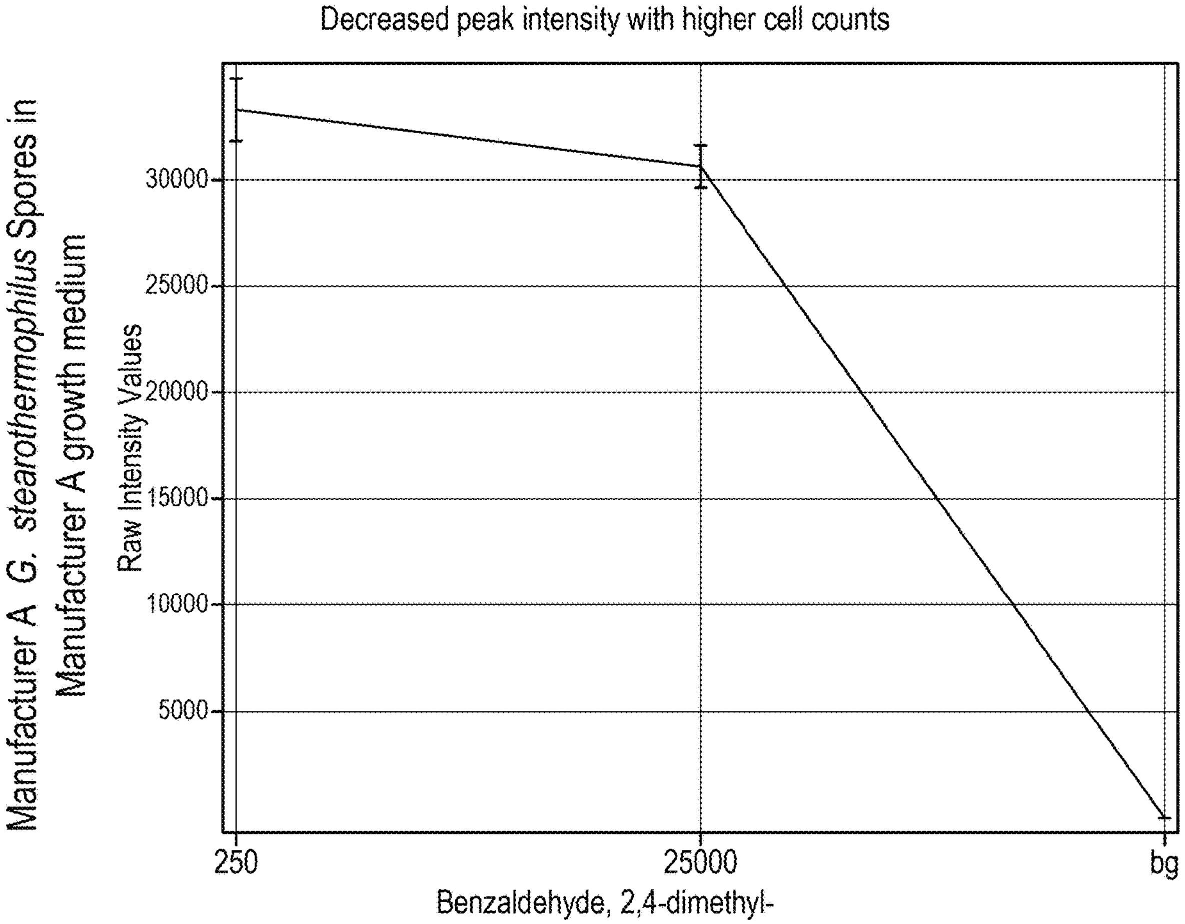
FIG. 8C illustrates the peak intensity by spore cell count of the VOC benzaldehyde, 2,4,-dimethyl- Manufacturer A *G. stearothermophilus* spores were in manufacturer A growth medium.
Figure 8D:
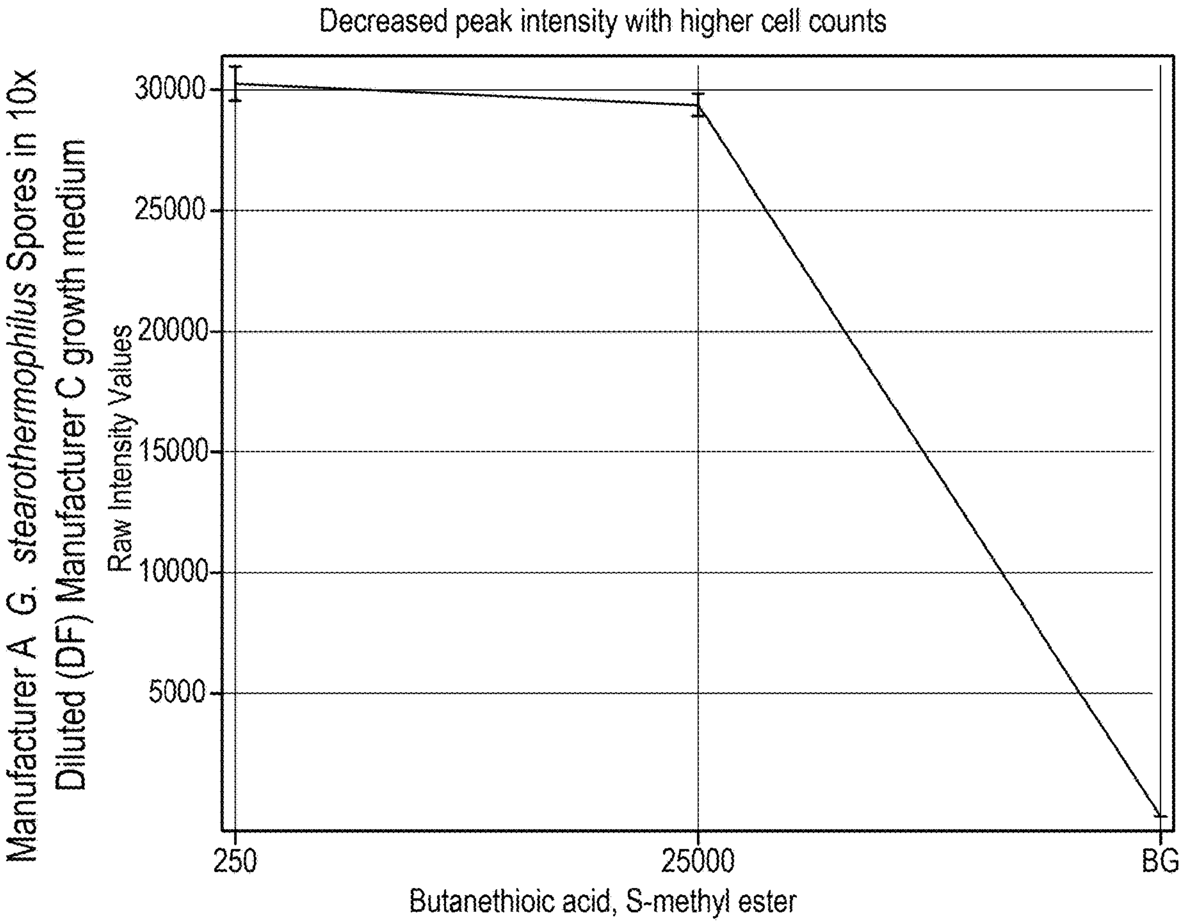
FIG. 8D illustrates the peak intensity by spore cell count of the VOC butanethioic acid, S-methyl ester when Manufacturer A *G. stearothermophilus* spores were in 10× diluted (DF) Manufacturer C growth medium.

In the following example, two levels of Manufacturer A *G. stearothermophilus* (steam) spores (250 cells and 25000 cells) were spiked in Manufacturer A growth medium and Manufacturer C diluted medium respectively. The total ion chromatograms (TIC) of backgrounds and spore-containing samples can be found in FIGS. 6 and 7. It can be seen that both the number of features and peak intensities are much higher in Manufacturer A grow medium compared to Manufacturer C 10-fold diluted medium. The number of features detected in the growth medium, and the spore-containing samples can be found in Table 3. Two selection criteria were used to extract VOCs released from spores: (a) the peak intensity in the spore-containing sample is at least 2-fold difference (either increase or reduced intensity) compared to negative; (b) this compound is present in above 80% of positive samples.

For the samples with higher cell counts (25,000), there are 47 unique spore VOCs in Manufacturer A growth medium compared to 26 VOCs from the samples prepared in Manufacturer C 10-fold diluted medium. For the samples with lower cell counts (250 cell), there are 53 unique spore VOCs in Manufacturer A growth medium compared to 32 VOCs from the samples prepared in Manufacturer C 10-fold diluted media. Some VOCs have higher peak intensities in the samples with lower cell counts and some of VOCs have lower peak intensities in the sample with higher cell counts. Examples of peak intensity comparisons from the samples with different level of spores can be found in FIGS. 8A-8D.

This study also indicated that it is possible to detect spore germination from the spores in the low hundred's concentration range.

Figure 9:
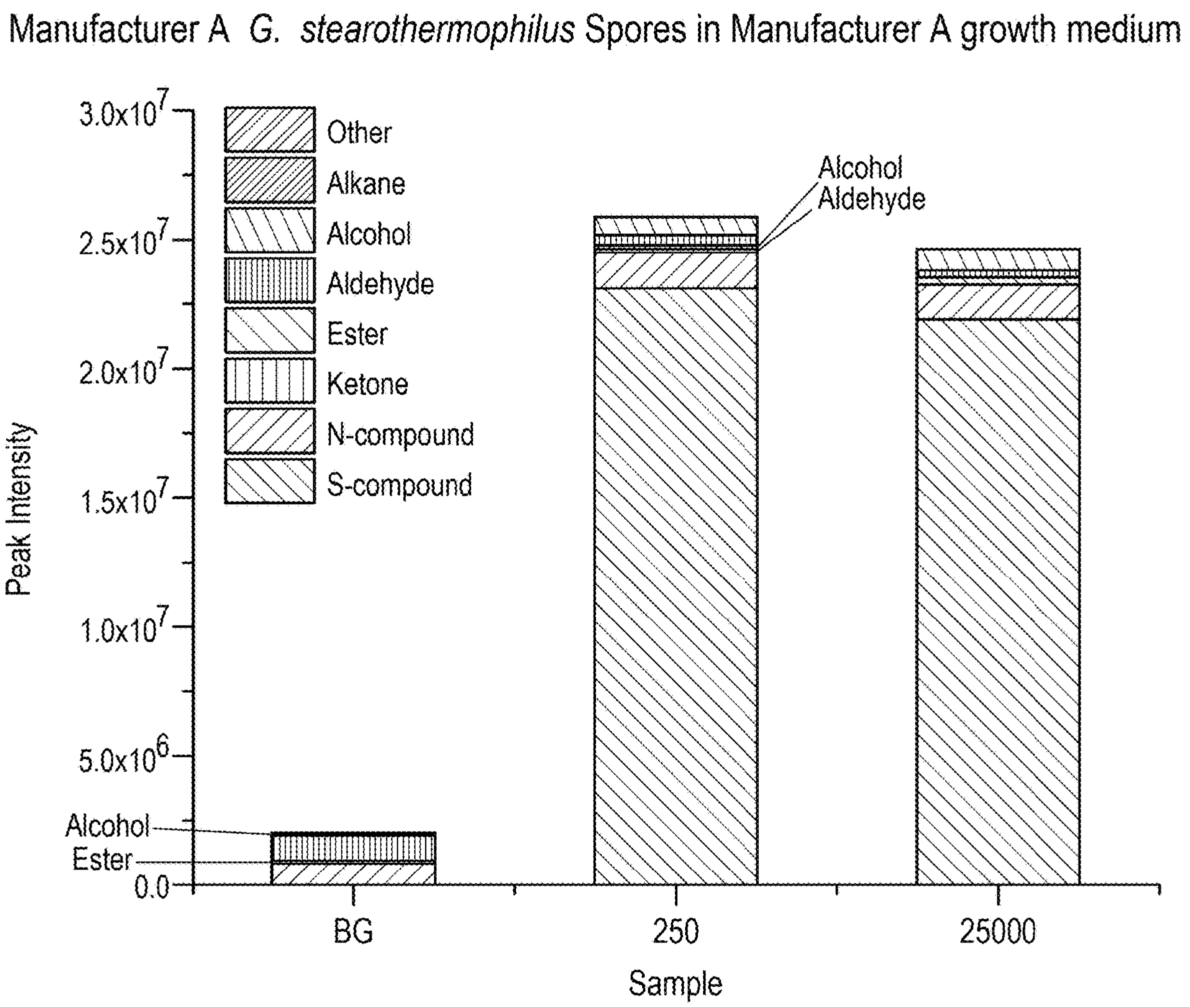
FIG. 9 is a graph illustrating the relative peak intensities from different groups of VOCs emitted from the background medium, 250 Manufacturer A *G. stearothermophilus* spores, and 25,000 Manufacturer A *G. stearothermophilus* spores in Manufacturer A growth medium.
Figure 10:
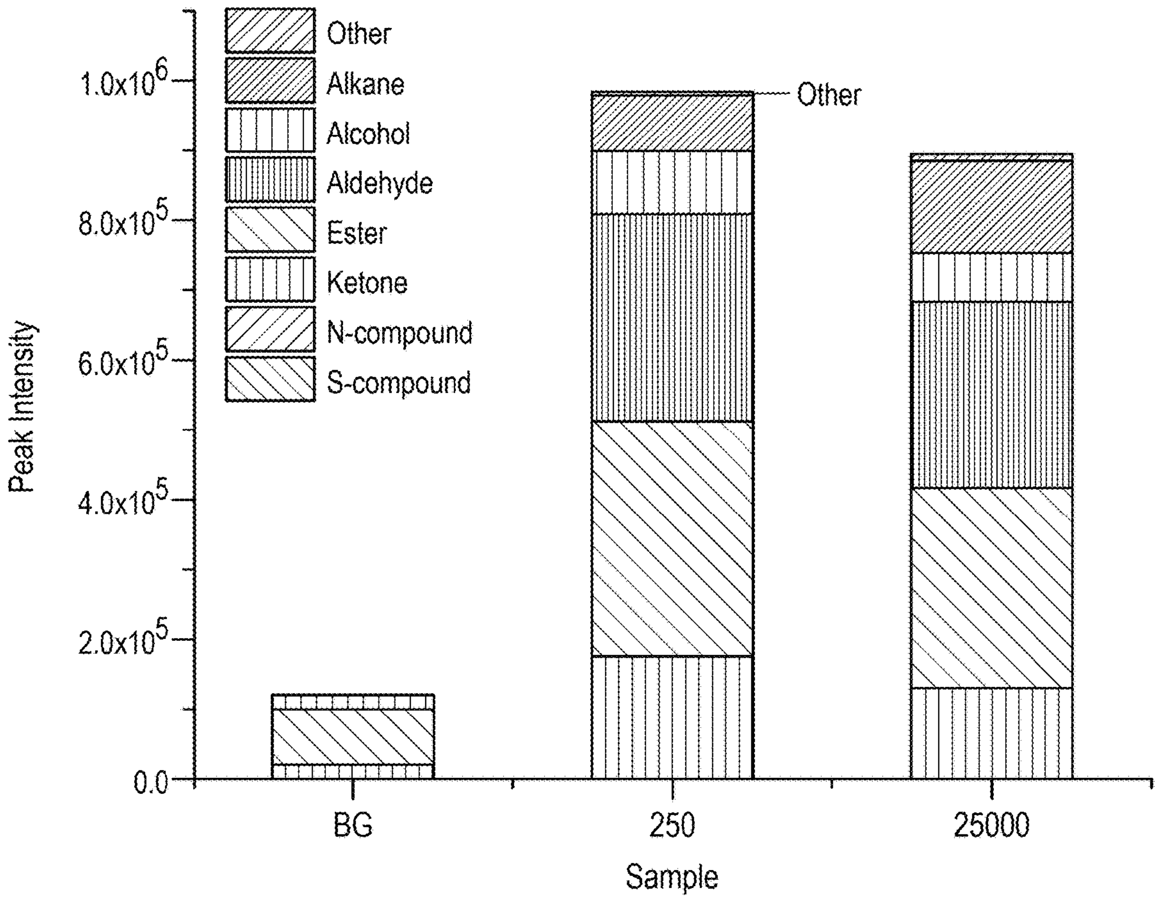
FIG. 10 is a graph illustrating the relative peak intensities from different groups of VOCs emitted from the background medium, 250 Manufacturer A *G. stearothermophilus* spores, and 25,000 Manufacturer A *G. stearothermophilus* spores in 10× diluted (DF) Manufacturer C growth medium.

The compositions of VOCs released from spores are also very different between growth medium types, as shown in FIGS. 9 and 10. Both the N-containing and the S-containing compounds are produced in larger quantities in the Manufacturer A growth medium positive samples compared to the Manufacturer C 10-fold diluted medium positive samples. This is in good agreement with the increased relative peak intensities for both S and N containing compounds identified in Manufacturer A growth medium. These results highlight the potential to produce the targeted spore VOCs by modifying the compositions of the growth medium.

For the positive samples prepared in Manufacturer C 10-fold diluted medium, results showed increased number of ketones, aldehyde and alcohols. Surprisingly, increased peak intensities in ester, aldehyde, and alcohol-based VOCs were observed in low range spore samples but not in the high range samples as shown in FIGS. 8A-8D.

TABLE 3

Number of compounds identified in the backgrounds and spore containing samples

| Sample | Number of compounds identified | Sample | Number of compounds identified |
|---|---|---|---|
| Manufacturer A background | 180 ± 17 | Manufacturer C 10× df GM background | 169 ± 10 |
| Manufacturer A GM + 250 spores (steam) | 211 ± 8 | Manufacturer C 10× df GM + 250 Manufacturer A spores (steam) | 173 ± 11 |
| Manufacturer A GM + 25,000 spores (steam) | 222 ± 10 | Manufacturer C 10× df GM + 25 000 Manufacturer A spores (steam) | 179 ± 18 |

Common spore related VOCs can be found in both growth medium are 3-Hexanone, 4-methyl 2-Heptanone, phorone in ketone family, 3-ethyl-benzaldehyde, 2,4-dimethyl-benzaldehyde in aldehyde family, 2,2,4-trimethyl-1,3-pentanediol diisobutyrate in ester, 3,6,6-trimethyl-bicyclo[3.1.1]hept-2-ene, 2,2,4,6,6-pentamethyl-heptane in alkane family.

Impact of Different Spores

Figure 11:
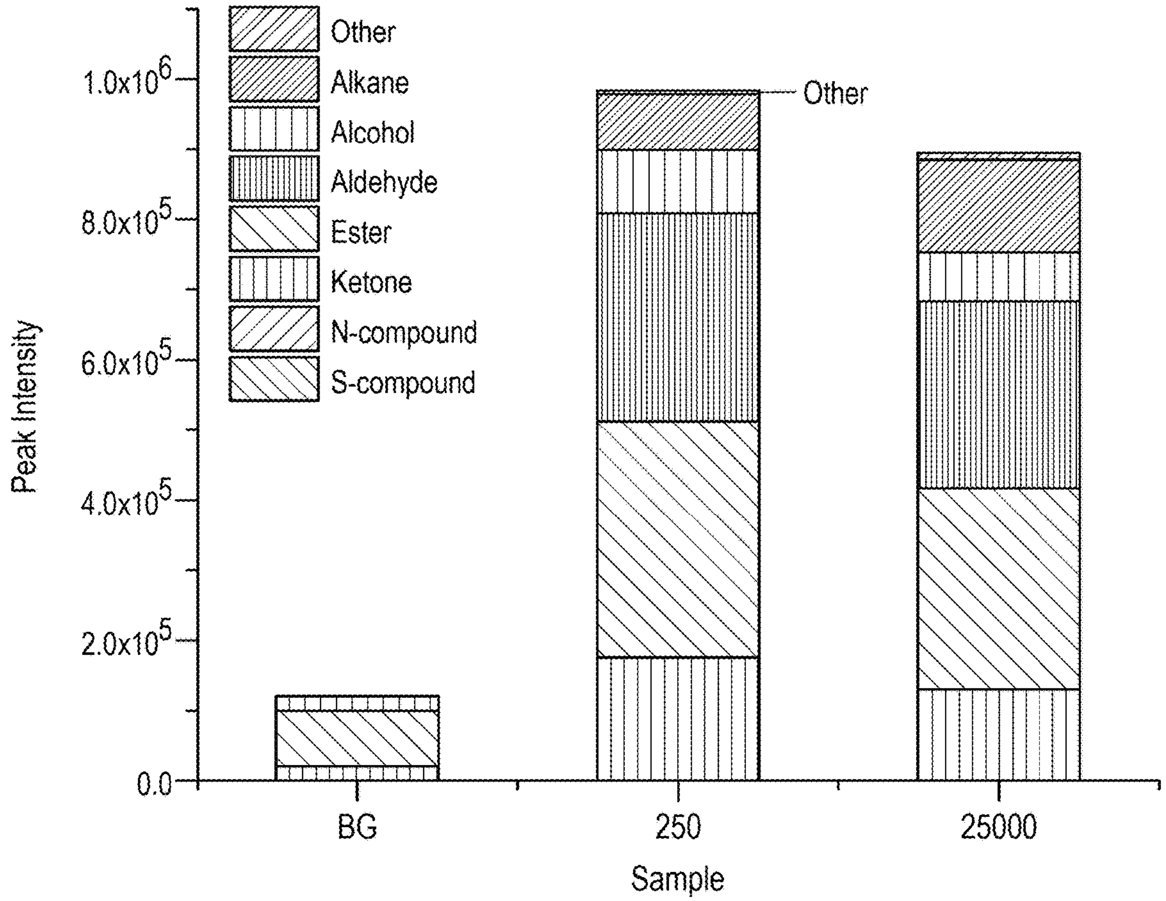
FIG. 11 is a graph illustrating the relative peak intensities from different groups of VOCs emitted from the background medium, 250 Manufacturer A *G. stearothermophilus* spores, and 25,000 Manufacturer A *G. stearothermophilus* spores in 10× diluted (DF) Manufacturer C growth medium.
Figure 12:
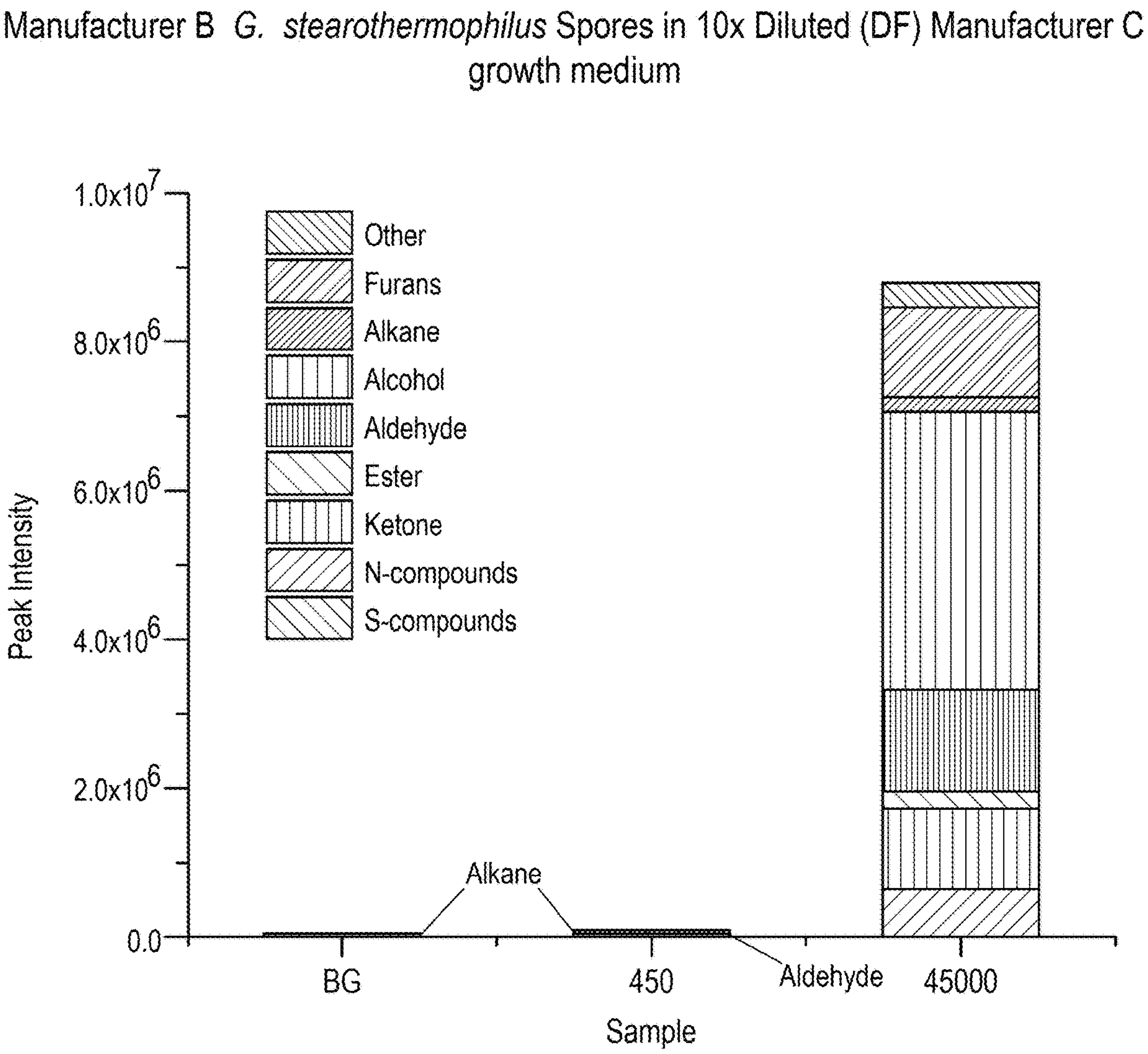
FIG. 12 is a graph illustrating the relative peak intensities from different groups of VOCs emitted from the background medium, 450 Manufacturer B *G. stearothermophilus,* and 45,000 Manufacturer B *G. stearothermophilus* spores in 10× diluted (DF) Manufacturer C growth medium.
Figure 13:
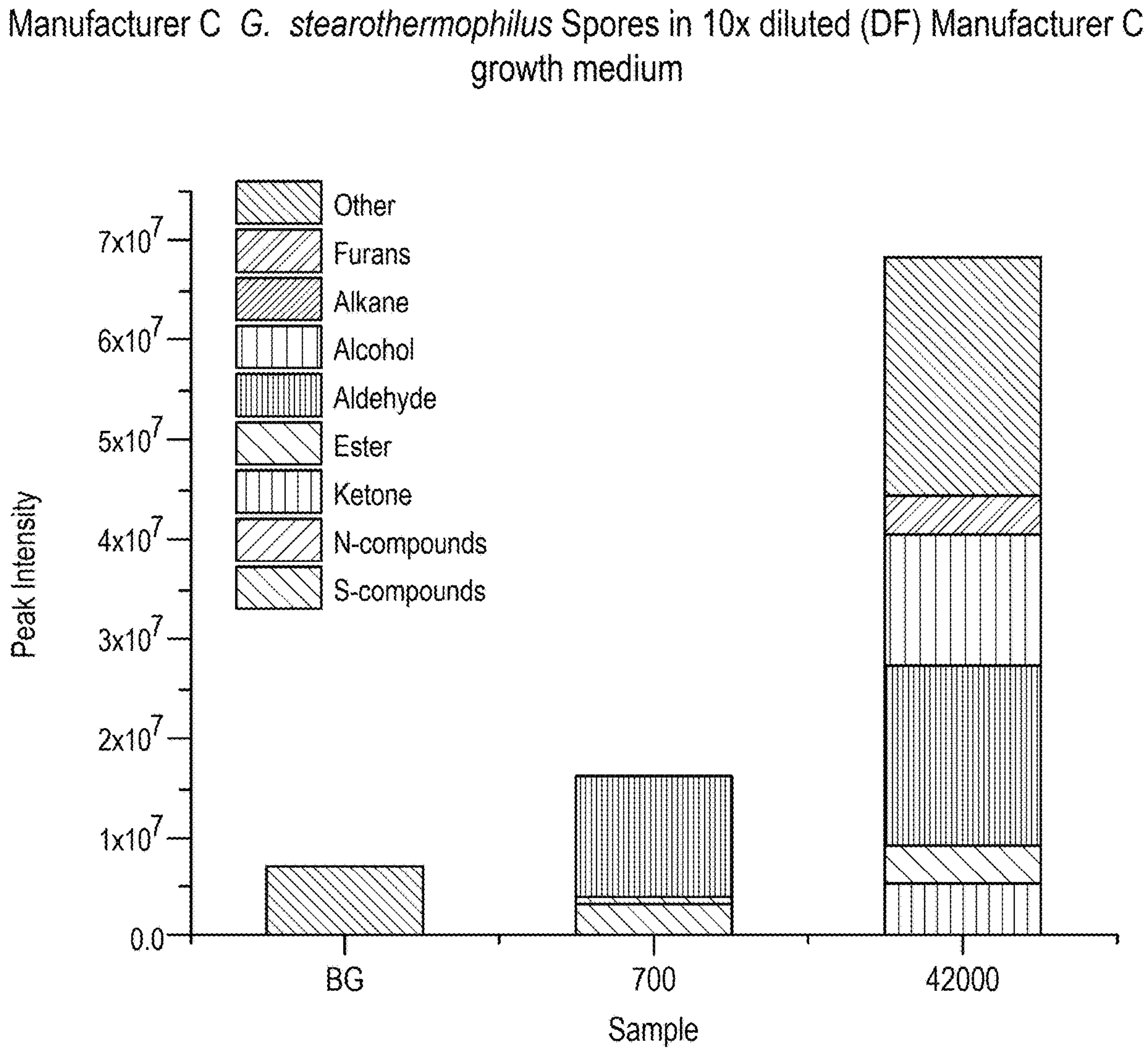
FIG. 13 is a graph illustrating the relative peak intensities from different groups of VOCs emitted from the background medium, 700 Manufacturer C *G. stearothermophilus* spores, and 42,000 Manufacturer C *G. stearothermophilus spores in* 10× diluted (DF) Manufacturer C growth medium.

For this study, spore samples for steam sterilization from Manufacturer a, B and C were prepared and spiked in Manufacturer C 10-fold diluted GM. Headspace VOCs from positive samples were collected and compared to the negative samples (headspace VOCs from Manufacturer C 10-fold diluted GM). The number of compounds identified in each group of samples can be found in Table 4. The comparison of the relative peak intensities from different groups of VOCs emitted from the background medium from three groups of spore samples can be found in FIGS. 11-13. Increased number of compounds were detected in the positive samples and more VOCs were obtained in the spore samples with a higher cell count. Based on the selection criteria to extract the spore VOCs, about 26, 80 and 26 spore associated VOCs were identified in Manufacturers A, B and C samples with higher cell counts respectively. The compositions and peak intensities of the VOCs produced from three spore groups can be found in FIGS. 11 to 13.

TABLE 4

Number of compounds identified in the backgrounds and spore containing samples

| Sample | Number of compounds identified | Sample | Number of compounds identified | Sample | Number of compounds identified |
|---|---|---|---|---|---|
| Manufacturer C 10-fold diluted GM Background | 169 ± 10 | Manufacturer C 10-fold diluted GM Background | 206 ± 7 | Manufacturer C 10-fold diluted GM Background | 217 ± 14 |
| Manufacturer C 10-fold diluted GM + 250 spores Manufacturer A (steam) | 173 ± 11 | Manufacturer C 10-fold diluted GM + spores Manufacturer B (steam) | 219 ± 11 | Manufacturer C 10-fold diluted GM spores Manufacturer C (steam) | 222 ± 9 |
| Manufacturer C 10-fold diluted GM + 25,000 spores Manufacturer A (steam) | 179 ± 18 | Manufacturer C 10-fold diluted GM + 45,000 spores Manufacturer B (steam) | 241 ± 11 | Manufacturer C 10-fold diluted GM + 42,000 spores Manufacturer C (steam) | 254 ± 26 |

Common VOCs can be found in all three type spore-containing samples including 2-pentanone, methyl Isobutyl Ketone, 3-hexanone, cyclohexanone, 4-methyl-2-heptanone, 6-methyl-3-heptanone in ketone family, 2-methyl-2-propanol, amylene hydrate, 2-methyl-1,3-pentanediol in alcohol family, acetic acid, pentyl ester, benzoic acid, methyl ester in ester, 2,4-dimethyl-benzaldehyde in aldehyde group, tetrahydro-2,2,5,5-tetramethyl-furan in furans. Table 5 summarizes the common VOCs identified associated with spore germination.

TABLE 5

Putative spore VOCs identified present in all three steam BI

| Compounds | CAS |
|---|---|
| 2-Propanol, 2-methyl- | 75-65-0 |
| Propane, 2-ethoxy-2-methyl- | 637-92-3 |
| Amylene hydrate | 75-85-4 |
| 2-Pentanone | 107-87-9 |
| 2-Butanol, 2,3-dimethyl- | 594-60-5 |
| Acetic acid, pentyl ester | 628-63-7 |
| Methyl Isobutyl Ketone | 108-10-1 |
| Furan, tetrahydro-2,2,5,5-tetramethyl- | 15045-43-9 |
| 2-Heptanone, 4-methyl- | 6137-06-0 |
| 2-tert-Butoxytetrahydrofuran | 1927-59-9 |
| 2-Octanol, 2-methyl- | 13254-34-7 |
| Ethanol, 2-(1,1-dimethylethoxy)- | 7580-85-0 |
| 1,3-Pentanediol, 2-methyl- | 149-31-5 |
| 3-Methoxy-3-methylbutanol | 56539-66-3 |
| Propanoic acid, 2-methyl-, 3-hydroxy-2,2,4-trimethylpentyl ester | 77-68-9 |
| 2,2,4-Trimethyl-1,3-pentanediol diisobutyrate | 6846-50-0 |

Spores for ethylene oxide and vapor hydrogen peroxide-based sterilization were obtained from Manufacturers A and B respectively. The spore suspensions were prepared in Manufacturer C 10-fold diluted GM and their headspace VOCs were studied, as shown in Table 6. An increased number of VOCs were detected in the spore-containing samples.

TABLE 6

Number of compounds identified in the backgrounds and spore containing samples

| Sample | Number of compounds identified | Sample | Number of compounds identified |
|---|---|---|---|
| Manufacturer C 10× diluted GM background | 175 ± 7 | Manufacturer C 10× diluted GM background | 124 ± 11 |
| Manufacturer C 10× diluted GM + 14,000 spores Manufacturer A Bat spores (ETO) | 182 ± 12 | Manufacturer C 10× diluted GM + 800 spores Manufacturer B Gst spores (VHP) | 119 ± 9 |
| | | Manufacturer C 10× diluted GM + 80,000 spores Manufacturer Gst B spores (VHP) | 134 ± 6 |

Impact of Sterilization on Spore VOC

Figure 14:
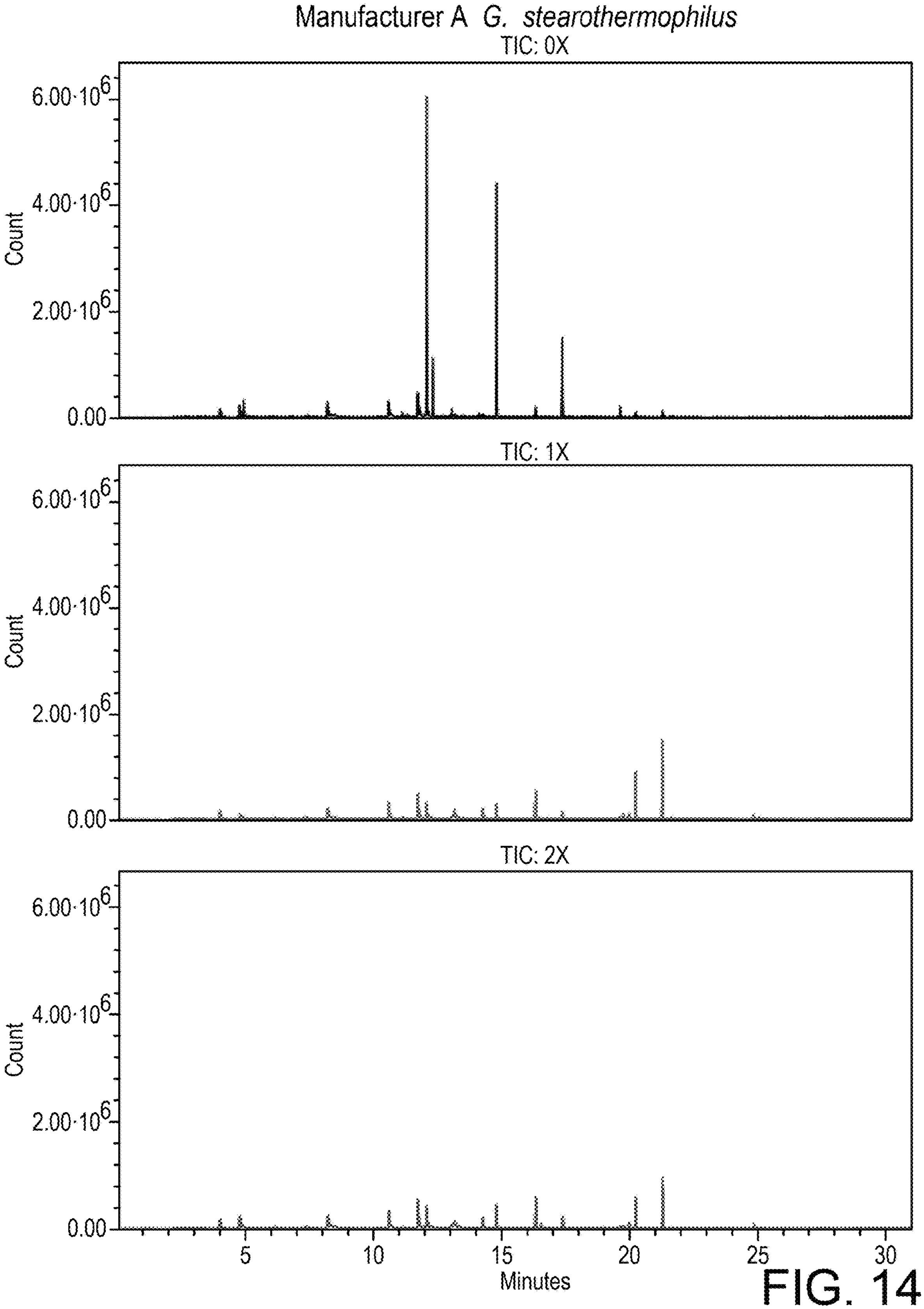
FIG. 14 illustrates three total ion chromatograms (TICs) collected from headspace VOCs from Manufacturer A *G. stearothermophilus* spores with after no steam sterilization, after 1× steam sterilization cycle (121° C. for 10 minutes), and after 2× steam sterilization cycles (121° C. for 10 minutes) in 10× diluted (DF) Manufacturer C growth medium.
Figure 15:
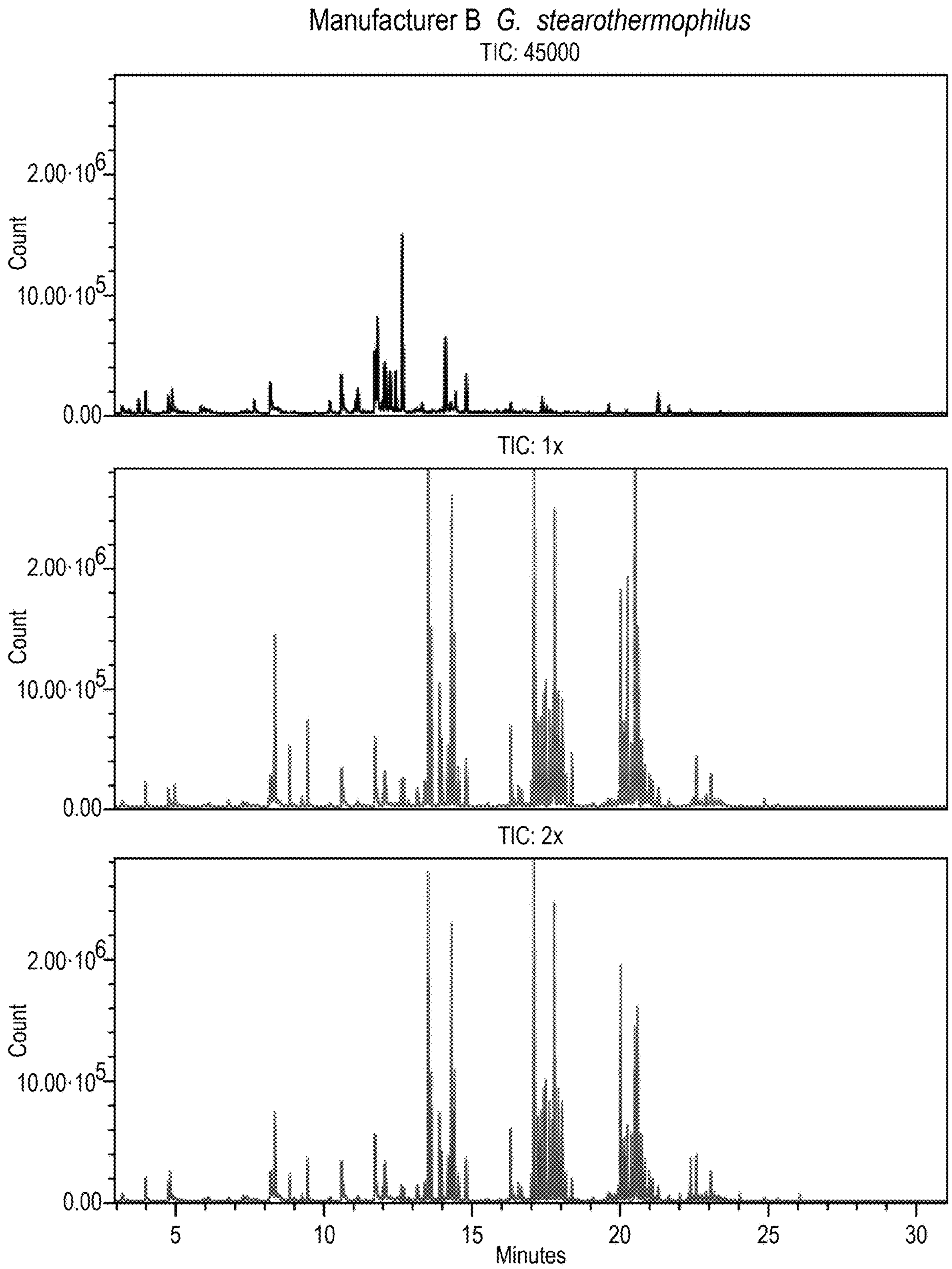
FIG. 15 illustrates three total ion chromatograms (TICs) collected from headspace VOCs from Manufacturer B *G. stearothermophilus* after no steam sterilization, after 1× steam sterilization, and after 2× steam sterilization in 10× diluted (DF) Manufacturer C growth medium.
Figure 16:
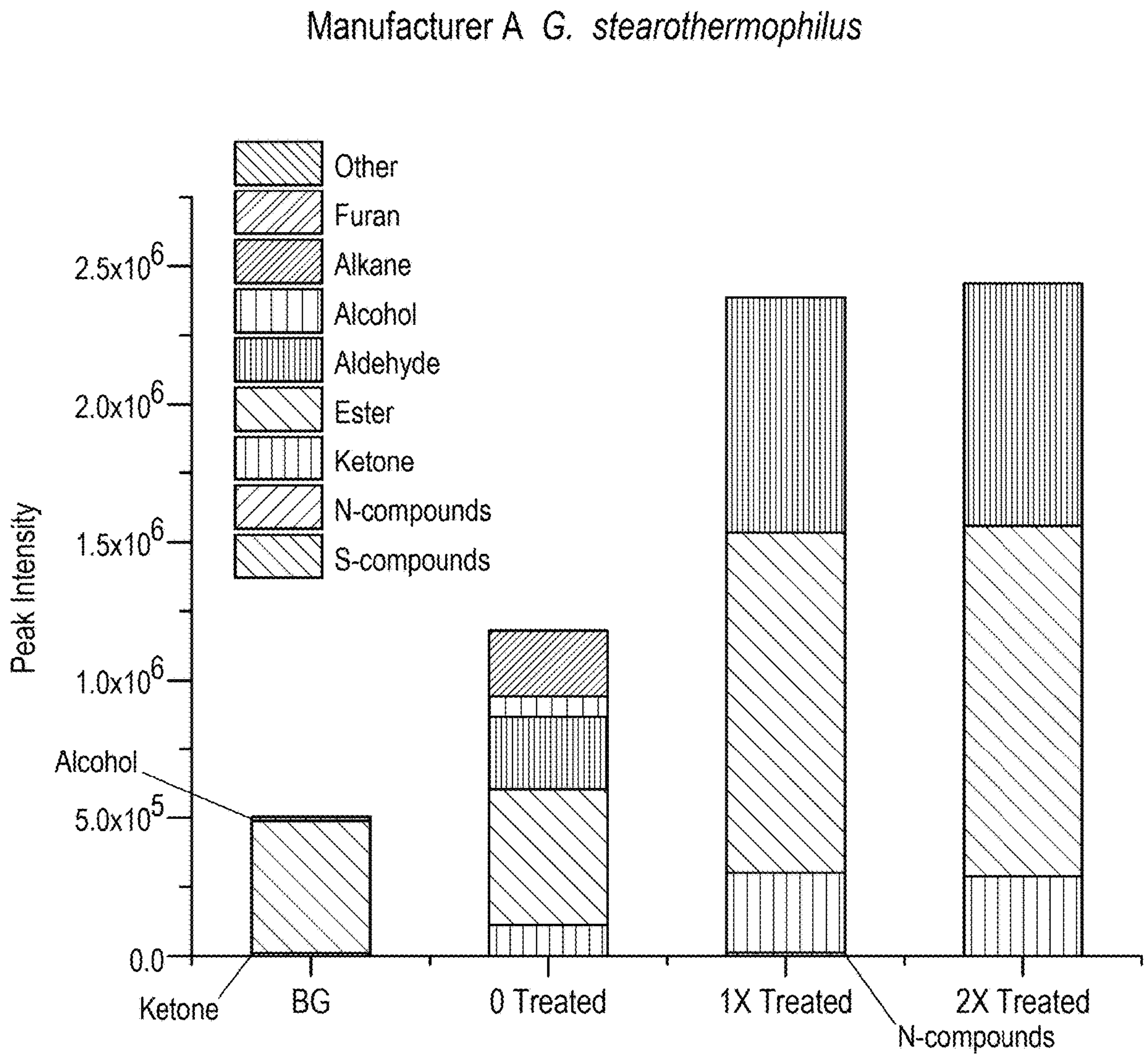
FIG. 16 is a graph illustrating the relative peak intensities from different groups of VOCs emitted from Manufacturer A *G. stearothermophilus* spores after no steam sterilization, after 1× steam sterilization, and after 2× steam sterilization in 10× diluted (DF) Manufacturer C growth medium.
Figure 17:
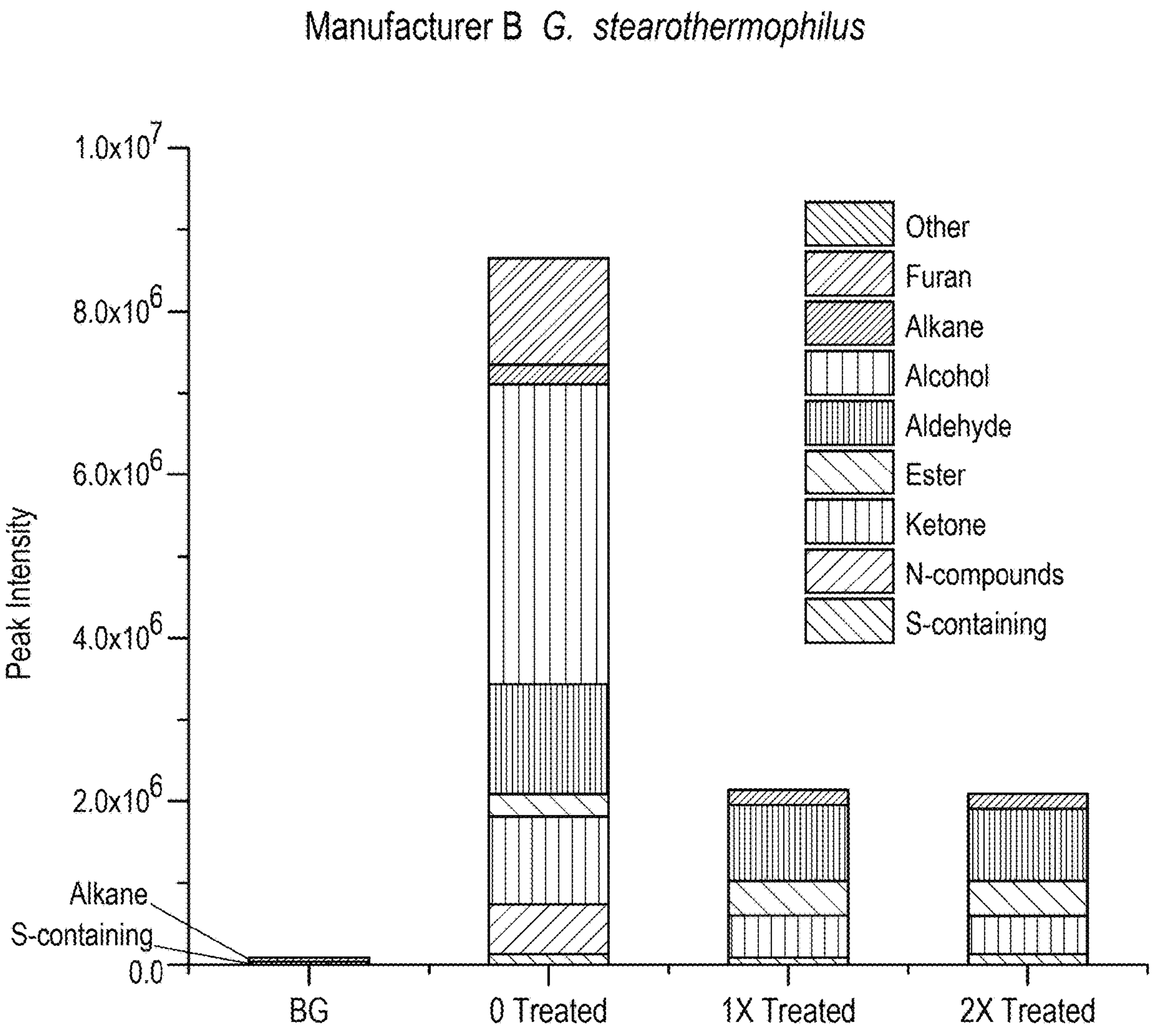
FIG. 17 is a graph illustrating the relative peak intensities from different groups of VOCs emitted from Manufacturer B *G. stearothermophilus* spores after no steam sterilization, after 1× steam sterilization, and after 2× steam sterilization in 10× diluted (DF) Manufacturer C growth medium.
Figure 18A:
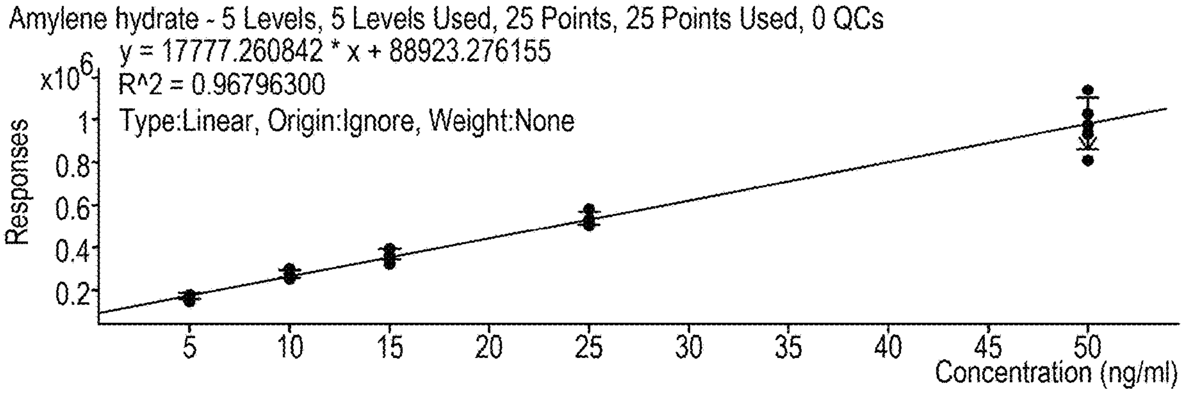
FIG. 18A illustrates the calibration curve for the VOC standard amylene hydrate, which was used to quantify the VOC produced from the tested spore suspensions.
Figure 18B:
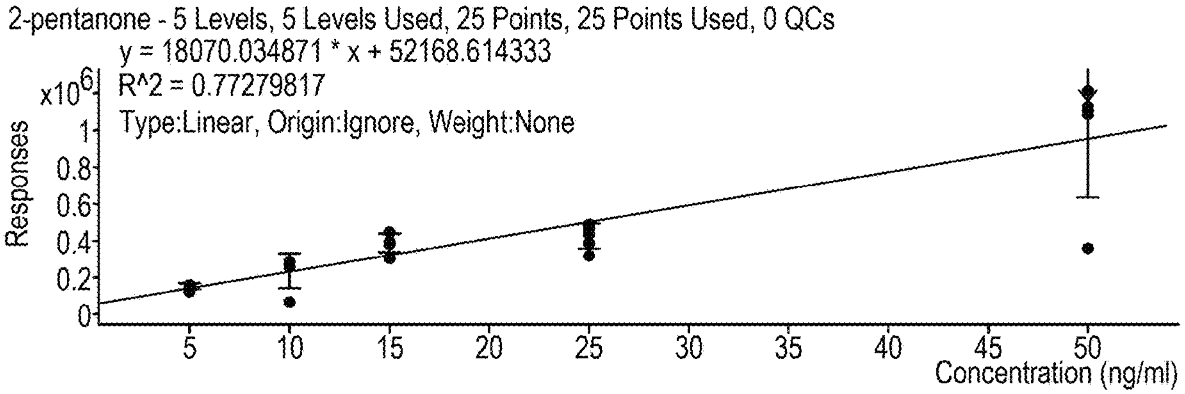
FIG. 18B illustrates the calibration curve for the VOC standard 2-pentanone, which was used to quantify the VOC produced from the tested spore suspensions.
Figure 18C:
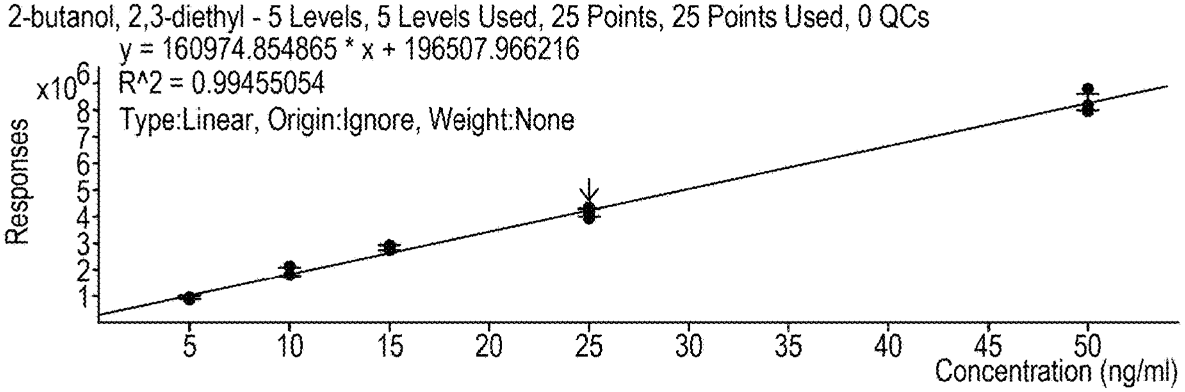
FIG. 18C illustrates the calibration curve for the VOC standard 2,3-dimethyl-2-butanol, which was used to quantify the VOC produced from the tested spore suspensions.
Figure 18D:
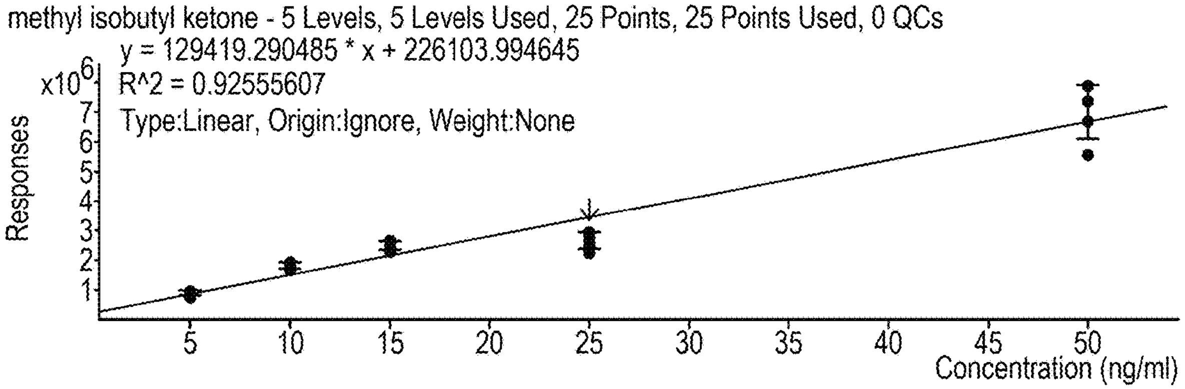
FIG. 18D illustrates the calibration curve for the VOC standard methyl isobutyl ketone, which was used to quantify the VOC produced from the tested spore suspensions.
Figure 18E:
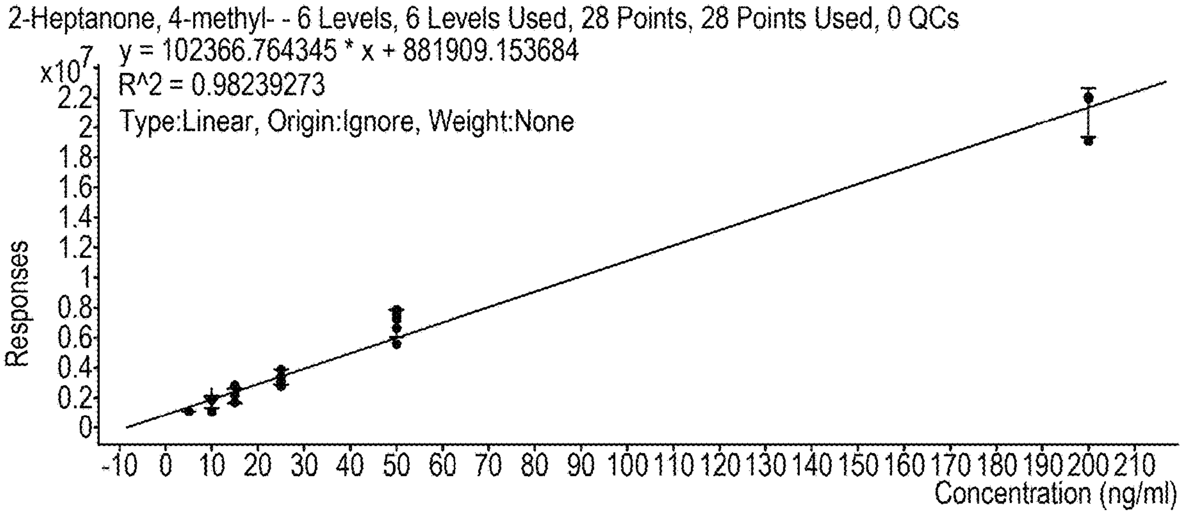
FIG. 18E illustrates the calibration curve for the VOC standard 4-methyl-2-heptanone, which was used to quantify the VOC produced from the tested spore suspensions.
Figure 20A:
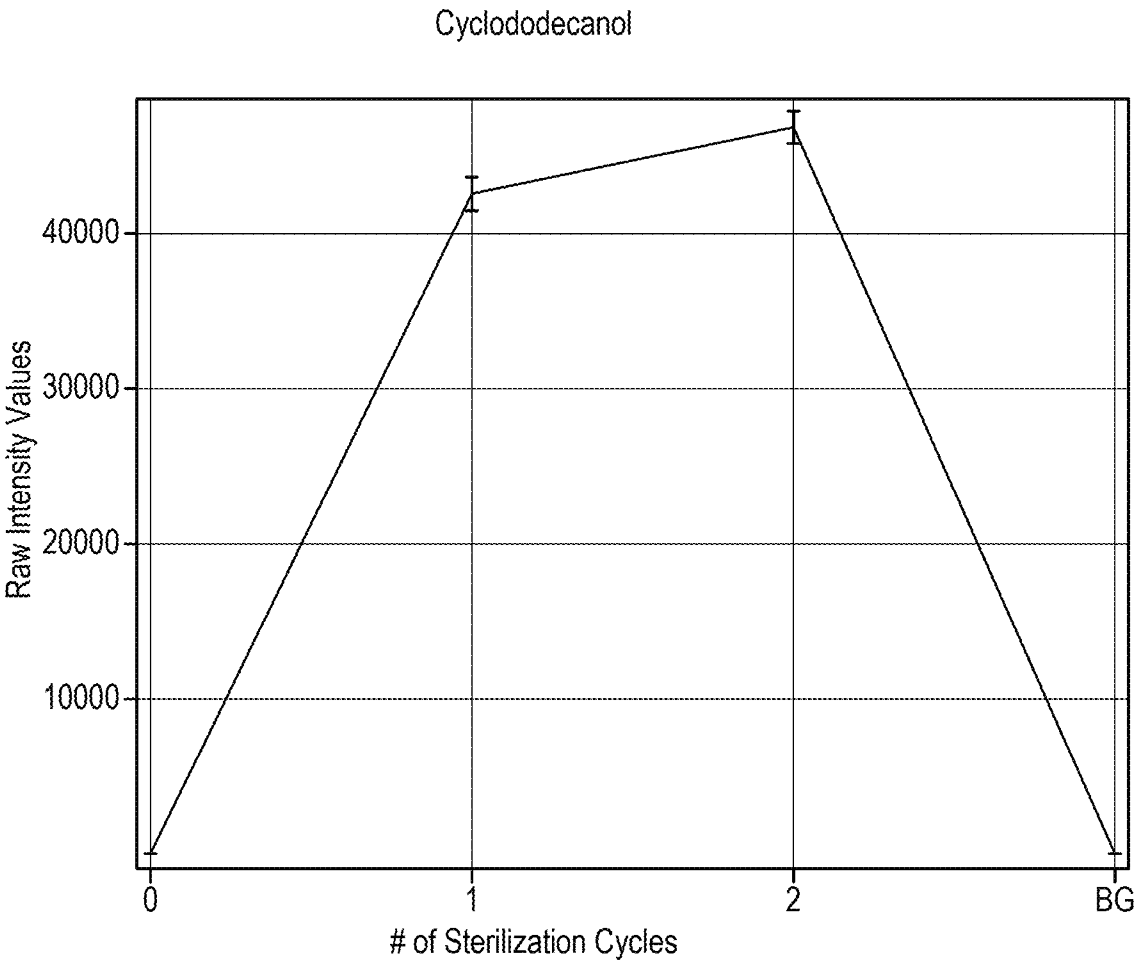
FIG. 20A is a graph illustrating the increase in peak intensity of cyclododecanol as the number of sterilization cycles in increased.
Figure 20B:
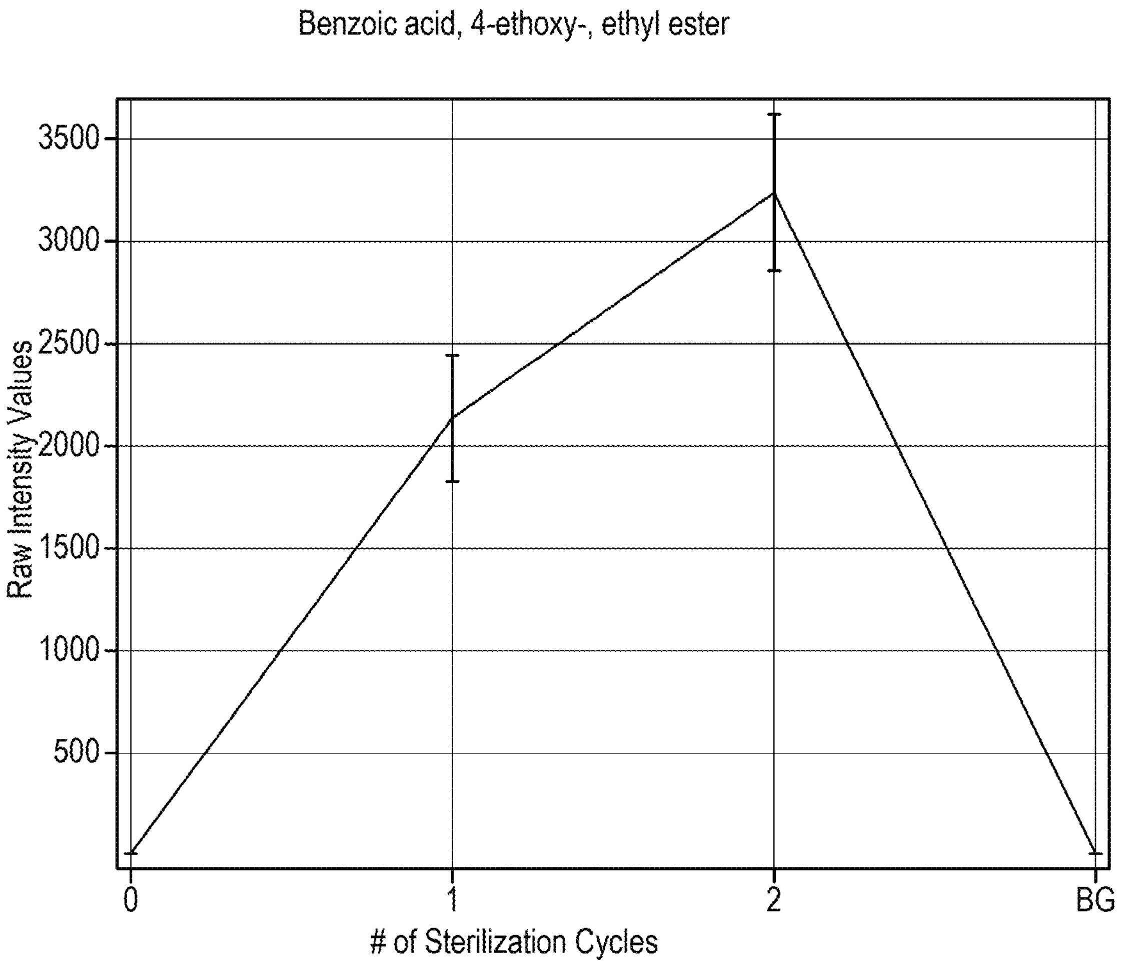
FIG. 20B is a graph illustrating the increase in peak intensity of benzoic acid, 4-ethoxy and ethyl ester as the number of sterilization cycles is increased.

Both Manufacturers A and B *G. stearothermophilus* spore (steam) samples were spiked in Manufacturer C 10-fold diluted GM. The stock spore suspensions were split into three groups. They were sterilized at 121° C. for 10 minutes for 0, 1 and 2 times respectively. The headspace of sterilized spore samples were collected and compared to the VOCs collected from untreated spore samples. The TIC of Manufacturers A and B spore samples with different sterilization treatment can be found in FIGS. 14 and 15 respectively. The number of identified compounds can be found in Table 7. An increased level of VOC emissions were detected in the sterilized samples. Some VOC intensities increased with an increased number of sterilization cycles as shown in FIGS. 20A and 20B, where the peak intensity of cyclododecanol and benzoic acid, 4-ethoxy and ethyl ester increased as the number of sterilization cycles increased. Thus, some VOC compounds can be used for sterilization confirmation including cyclododecanol; benzoic acid, 4-ethoxy-, ethyl ester; and 3,4,4-trimethyl-3-pentanol.

TABLE 7

Number of compounds identified in spore samples before and after sterilization

| Sample | Number of compounds identified | Sample | Number of compounds identified |
|---|---|---|---|
| Manufacturer A spores without sterilization treatement | 179 ± 18 | Manufacturer B spores without sterilization treatement | 241 ± 11 |
| Manufacturer A spores with sterilization treatement once | 217 ± 6 | Manufacturer B spores with sterilization treatement once | 292 ± 15 |
| Manufacturer A spores with sterilization treatement twice | 210 ± 5 | Manufacturer B spores with sterilization treatement twice | 278 ± 40 |

Spore VOC Validation and Quantification

Due to the availabilities of VOC standards, only a small number of common VOCs were validated. Stock VOCs were prepared by weighing about 20 mg of standard in 10 ml of HPLC grade methanol in a volumetric flask. Series dilutions were prepared to have VOC standards in the concentration of 0, 5, 10, 15, 25, 50 ppb in Manufacturer C 10-fold diluted GM. Identical SPME VOC extraction and GC/MS parameters were used for VOC standards measurement. Both retention time and mass spectra are used for a compound validation. Validated spore VOCs are listed in Table 8. The calibration curves of example VOC standards can be found in FIGS. 18A-18E. They were used to quantify the amount of VOCs produced from spore suspensions including 48000 cells of Manufacturer A *G. stearothermophilus* spores (steam). 24,000 of Manufacturer B *G. stearothermophilus* spores (steam), 42,000 Manufacturer C *G. stearothermophilus* spores (steam), and 14,000 of Manufacturer A *B. atrophaeus* spores (ethylene oxide) in Manufacturer C 10-fold diluted GM. The quantification results on spore VOCs released from different spore samples can be found in Table 9.

TABLE 8

Validated spore VOC with matched retention time and mass spectra are listed.

| Compounds | Retention time in VOC standards (min) | Retention Time in Spore VOC (min) |
|---|---|---|
| 2-Propanol, 2-methyl- | 1.56 | 1.56 |
| Propane, 2-ethoxy-2-methyl- | 2.04 | 2.04 |
| Amylene hydrate | 2.18 | 2.19 |
| 2-Pentanone | 2.72 | 2.72 |
| 2-Butanol, 2,3-dimethyl- | 3.38 | 3.47 |
| Methyl Isobutyl Ketone | 3.62 | 3.66 |
| Furan, tetrahydro-2,2,5,5-tetramethyl- | 4.12 | 4.15 |

TABLE 9

Level of VOCs produced from different type of spores can be found without requiring enzymatic or fluorescence modification.

| | | Spore Manufacturer | | | |
|---|---|---|---|---|---|
| VOC Standards | RT (min) | A (steam) (ppb) | B (steam) (ppb) | C (steam) (ppb) | A (EtO) (ppb) |
| 2-propanol, 2-methyl | 1.56 | 151.16 ± 48.89 | 309.81 ± 87.95 | 61.55 ± 24.65 | 231.58 ± 89.35 |
| Amylene hydrate | 2.18 | 24.36 ± 6.19 | 41.70 ± 7.01 | 24.77 ± 5.93 | 11.03 ± 4.37 |
| 2-pentanone | 2.72 | 5.24 ± 1.42 | 32.21 ± 4.13 | 12.83 ± 8.72 | 5.69 ± 1.39 |
| 2-butanol, 2,3-diethyl | 3.36 | 3.56 ± 1.89 | 4.94 ± 0.41 | 3.94 ± 2.35 | 3.12 ± 2.64 |
| Methyl Isobutyl Ketone | 3.63 | 1.57 ± 1.18 | 3.20 ± 0.24 | 1.36 ± 0.74 | 0.72 ± 0.10 |
| Furan, tetrahydro-2,2,5,5-tetramethyl- | 4.15 | 2.38 ± 0.47 | 3.37 ± 0.28 | 1.15 ± 0.77 | 0.81 ± 0.18 |
| 2-Heptanone, 4-methyl- | 9.18 | 2.59 ± 0.66 | 68.28 ± 4.25 | 27.53 ± 27.15 | 4.75 ± 1.68 |
| 2,2,4-Trimethyl-1,3-pentanediol diisobutyrate | 19.32 | 6.09 ± 2.11 | 4.64 ± 1.83 | 5.21 ± 1.23 | 1.65 ± 0.66 |

Discussion

Microorganisms produce a large diversity of small molecules, like volatile compounds as secondary metabolic byproducts, during the entire growth cycles. Volatile organic compounds (VOCs) are carbon-based compounds with low molecular weight and generally, high vapor pressure; because of their nature, they spread easily in the environment. The higher the volatility (lower the boiling point). the more likely the compound will be emitted from a product, medium, or surface into the air. VOCs have been reported to be involved in microbial interactions. The chemical composition of the bacterial volatilome is defined by genetic determinants and can be used as a chemotaxonomic marker in standardized conditions. Microorganisms can also emit induced volatiles that are triggered by biological interactions or environmental cues. The underlying biosynthetic pathways generating the VOCs include heterotrophic carbon metabolism, fermentation, amino-acid catabolism, fatty acid degradation, sulfur reduction or terpenoid biosynthesis. Some VOCs are regularly produced by a wide range of micro-organisms, while other VOCs can be exclusively produced by specific strains.

Potential Metabolic Pathway for VOC Production

Metabolism of exogenous and endogenous compounds begins soon after initiation of spore germination, and much of the spore's energy needed in the 10 to 15 minutes after initiation of germination can be met by catabolism of molecules stored in the dormant spore.

Dormant spores have a significant amount of NAD and NADP, but no NADH or NADPH, and extremely low level of other common energy compounds such as ATP. During the first minute of spore germination, active metabolic pathways will mostly lead to ATP production and nicotinamide nucleotide reduction (ex: NAD and NADP conversion to NADH and NADPH). These pathways are mostly anaerobic for the first 5 minutes of the germination process, then the aerobic pathways start to be used.

Germination spore will probably use internal energy and carbon sources. Glutamate, malate, arginine, sulfolactic acid, 3-phospho glycerate are some of the organic compounds that were identified inside the spores. Sporulation conditions (sporulation medium, temperature, etc.) influence the spore contents and sterilization resistance.

In addition, pyridine-2,6-dicarboxylic acid, and peptidoglycan fragment (N-acetyl muramic acid and N-acetyl-D-glucosamine) will be release in the growth medium at the beginning of the germination as well as amino acid generated by proteolysis of small acid-soluble spore proteins.

Furthermore, the enzyme active in the coat or outer membrane of the spore may react with external compounds for activation of the germination process (ex: glucose or alanine-based compounds). Growth medium pH can also influence the VOC produced. BI growth medium is buffered at about pH 6.8-7.2, limiting the pH influence.

In studies on VOC produces by microorganism, it was demonstrated that esters were detected during anaerobic metabolism, in the presence of glucose or alcohols. If peptone was added, organic sulfur volatiles were detected. The VOC produced are also dependent of the electron donor and acceptor Spore forming bacteria may produce the following compounds under anaerobic conditions:

- Acids: formic (PubChem #284), acetic (#176), caproic (#8892), isocaproic (#12587), valeric (#7991), isovaleric (#10430), acrylic (#6581), butyric (#264), isobutyric (#6590), propionic (#1032), and crotonic (#637090);
- Alcohols: 2,3-butanediol (#262), methanol (#887), ethanol (#702), isobutanol (#6560), isopentanol (#31260);
- Others: acetoin (#179).

Fatty acids and respective derivatives such as alkanes, alkenes, aldehydes, ketones, alcohols, as well as ethers and esters are most likely products of incomplete oxidations of the primary metabolism. However, typical secondary metabolites are found in the groups of terpenes, aromatic compounds, furans, and S- and N-containing compounds Importance of the Growth Medium As shown in this example, the growth medium will impact the types of VOCs observed. It has been observed that when peptone is added to growth medium, sulfur organic volatil were detected. Based on the quantity of S-coumpounds detected in the growth medium of Manufacturer A, it would confirm the presence of bacteriological peptone in it. In comparison, the Manufacturer C growth medium is a modified soybean casein digest broth with a pH indicator. This one may contain less easily available sulfur compounds in it since esters and aldehydes VOC were predominant.

Potential Pathway Leading to VOC

Figure 19:
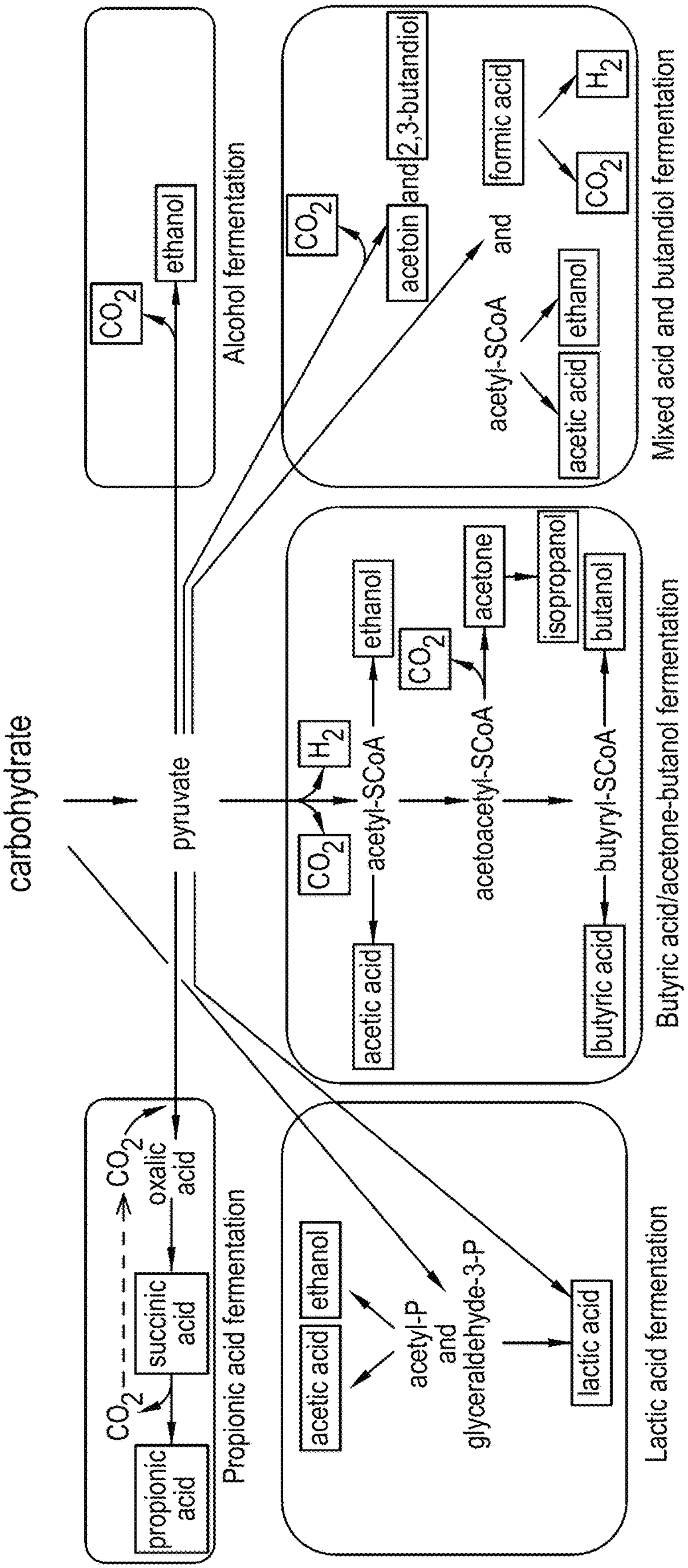
FIG. 19 is a flowchart illustrating VOC production during fermentation.

Determining the metabolic pathways leading to the VOC detected is challenging. The pathways described in FIG. 19 are known. However, since spores are searching to reduce the nucleoside such NAD+ in NADH at the beginning of the germination process, by product of the fermentation process such as butanol will be oxidized in butanal. This may happen with other fermentation by-product.

Some enzymes may only be active during the first few minutes of the spore germination, thus making them hard to detect. Only the metabolism by-products are detected.

One of the VOC identified in Table 9 of the GCMS study, the 2-propanol 2-methyl, can be produced by the Tert-Butyl methyl ether (MTBE) pathway. This pathway was identified in many bacterial species. For the other VOC, there is no direct metabolic pathway that were identified.

In general, sulfur-containing VOCs are formed through metabolism of sulfur-containing amino acids, for example, via, transamination, demethiolation or a recombination pathway.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for determining if a spore in a self-contained biological indicator is in a germination phase, the method comprising:

subjecting a self-contained biological indicator to a sterilization process, wherein the self-contained biological indicator comprises spores of *Geobacillus stearothermophilus* or *Bacillus atrophaeus;* exposing spores in the self-contained biological indicator to a growth medium;

incubating the spores in the self-contained biological indicator;

sampling headspace in the self-contained biological indicator; and determining if a volatile organic compound attributable to the germination phase of the spores in the biological indicator is released into headspace upon contact with the growth medium, wherein the presence of the volatile organic compound attributable to the germination phase of the spores in the self-contained biological indicator indicates failure of the sterilization process, wherein the volatile organic compound attributable to the germination phase of the self-contained biological indicator comprises an alkane, an alcohol, an ester, a ketone, a furan, or a combination thereof, wherein the alkane comprises 2,2,4,6,6-pentamethyl-heptane; the ketone comprises 2-pentanone, methyl isobutyl ketone, or 4-methyl-2-heptanone, the alcohol comprises 2-methyl-2- propanol, amylene hydrate, or 2-methyl-1,3-pentanediol; the ester comprises 3-hydroxy-2,4,4-trimethylpentyl 2-methylpropanoate, 2,2, 4-Trimethyl-1, or 3-pentanediol diisobutyrate; and the furan comprises tetrahydro-2,2,5,5-tetramethyl-furan.

2. The method of claim 1, wherein determining if a volatile organic compound is released into headspace from the growth medium comprises collecting an air sample from the headspace for volatile organic compound analysis.

3. The method of claim 2, wherein the air sample is collected and analyzed in a time frame of less than about 60 minutes.

4. The method of claim 1, wherein the sampling occurs within the self-contained biological indicator.

5. The method of claim 1, wherein the sampling occurs outside the self-contained biological indicator.

6. The method of claim 1, wherein the sterilization process is a steam sterilization process.

7. The method of claim 1, wherein the sterilization process is a vaporized hydrogen peroxide sterilization process.

8. The method of claim 1, wherein the sterilization process is an ethylene oxide sterilization process.

9. The method of claim 1, wherein the growth medium comprises tryptic soy broth or modified soybean casein digest broth.

10. The method of claim 1, wherein the volatile organic compound is polar.

11. The method of claim 1, further comprising applying a correction factor to remove any background volatile organic compounds attributable to the growth medium rather than the spores in the self-contained biological indicator in the germination phase.

12. The method of claim 1, wherein the self-contained biological indicator comprises a target level of spores to achieve a desired resistance in the self-contained-biological indicator depending on a type of sterilization process in which the self-contained biological indicator is utilized.

13. The method of claim 1, wherein the presence of the volatile organic compound is determined directly without the use of enzymatic reagents.

14. The method of claim 1, wherein the presence of the volatile organic compound is determined directly without the use of a fluorescence moiety.

15. The method of claim 1, wherein determining if a volatile organic compound attributable to the germination phase of the spore in the biological indicator is released into headspace upon contact with the growth medium involves comparing a measured volatile organic compound level with a control volatile organic compound level.

16. The method of claim 15, wherein it is determined that a volatile organic compound attributable to the germination phase of the spore in the biological indicator is released into headspace upon contact with the growth medium if the measured volatile organic compound level is higher than the control volatile organic compound level.

* * * * *